US011573235B2

(12) United States Patent
Seppo et al.

(10) Patent No.: US 11,573,235 B2
(45) Date of Patent: Feb. 7, 2023

(54) METHODS FOR GENERATING AN IMAGE OF A BIOLOGICAL SAMPLE

(71) Applicant: Leica Microsystems CMS GmbH, Wetzlar (DE)

(72) Inventors: Antti E. Seppo, Niskayuna, NY (US); Fiona Ginty, Niskayuna, NY (US); Kevin B. Kenny, Niskayuna, NY (US); David Lavan Henderson, Niskayuna, NY (US); Michael J. Gerdes, Niskayuna, NY (US); Adriana Ines Larriera, Niskayuna, NY (US); Xiaofeng Liu, Niskayuna, NY (US); Alex D. Corwin, Niskayuna, NY (US); Stephen E. Zingelewicz, Niskayuna, NY (US); Thomas Ha, Aliso Viejo, CA (US); Natalia R. Jun, Aliso Viejo, CA (US); Ainura Kyshtoobayeva, Aliso Viejo, CA (US); Denise A. Hollman-Hewgley, Aliso Viejo, CA (US); Ying Li, Niskayuna, NY (US)

(73) Assignee: LEICA MICROSYSTEMS CMS GMBH, Wetzlar (DE)

(*) Notice: Subject to any disclaimer, the term of this patent is extended or adjusted under 35 U.S.C. 154(b) by 488 days.

(21) Appl. No.: 14/388,057

(22) PCT Filed: Mar. 21, 2013

(86) PCT No.: PCT/US2013/033286
§ 371 (c)(1),
(2) Date: Sep. 25, 2014

(87) PCT Pub. No.: WO2013/148458
PCT Pub. Date: Oct. 3, 2013

(65) Prior Publication Data
US 2015/0050650 A1 Feb. 19, 2015

Related U.S. Application Data

(60) Provisional application No. 61/618,282, filed on Mar. 30, 2012.

(51) Int. Cl.
C12Q 1/68 (2018.01)
G01N 33/58 (2006.01)
C12Q 1/6841 (2018.01)
G01N 33/68 (2006.01)
G06V 20/69 (2022.01)
C12Q 1/6816 (2018.01)
G06T 7/00 (2017.01)

(52) U.S. Cl.
CPC ......... G01N 33/582 (2013.01); C12Q 1/6816 (2013.01); C12Q 1/6841 (2013.01); G01N 33/6803 (2013.01); G06T 7/0012 (2013.01); G06V 20/695 (2022.01); G06T 2207/10064 (2013.01); G06T 2207/30096 (2013.01)

(58) Field of Classification Search
None
See application file for complete search history.

(56) References Cited

U.S. PATENT DOCUMENTS

| 5,674,884 | A | 10/1997 | Booher et al. | |
|---|---|---|---|---|
| 7,629,125 | B2 | 12/2009 | Sood et al. | |
| 8,036,462 | B2 | 10/2011 | Can et al. | |
| 2003/0219767 | A1* | 11/2003 | Ayers | C12Q 1/6886 435/6.14 |
| 2004/0136969 | A1* | 7/2004 | Hussain | A61K 38/193 424/93.7 |
| 2007/0224625 | A1* | 9/2007 | Hainfeld | C12N 9/0065 435/6.12 |
| 2008/0137937 | A1* | 6/2008 | Athelogou | G06K 9/0014 382/133 |
| 2008/0138816 | A1* | 6/2008 | Brawley | B82Y 5/00 435/6.16 |

(Continued)

FOREIGN PATENT DOCUMENTS

| EP | 2049678 A2 | 4/2009 |
|---|---|---|
| EP | 2082226 B1 | 8/2011 |

(Continued)

OTHER PUBLICATIONS

Ko, "Hominin interbreeding and the evolution of human variation," Journal of Biological Research—Thessaloniki, 2016, 9 pages.*
"Viruses" (Wikipedia.com, accessed Nov. 24, 2012).*
"How many species of bacteria are there" (wisegeek.com; accessed Jan. 21, 2014).*
"Plant," (Wikipedia.com; accessed Aug. 28, 2015).*
"Mammal," (Wikipedia.com; accessed Sep. 22, 2011).*
"Murinae," (Wikipedia.com, accessed Mar. 18, 2013).*
"Fish," (Wikipedia.com, accessed Nov. 2, 2014).*

(Continued)

Primary Examiner — Bradley L. Sisson
(74) Attorney, Agent, or Firm — Leydig, Voit & Mayer, Ltd.

(57) ABSTRACT

A method for generating an image of a region of interest in a biological sample comprising the steps of: generating a first image including the region of interest of the biological sample having undergone a first protocol but not a second protocol; and generating a second image including the region of interest of the biological sample after having undergone a second protocol; wherein the region of interest is smaller than said sample. Also provided is a method of analyzing a biological sample, comprising providing an image of the biological sample according to the method for generating an image of a region of interest in a biological sample, and analyzing the biological sample from the image. Further provided are system and kit that comprise the means for executing the novel methods.

11 Claims, 5 Drawing Sheets

(56) References Cited

U.S. PATENT DOCUMENTS

| | | | |
|---|---|---|---|
| 2009/0258365 A1* | 10/2009 | Terstappen | C12Q 1/6886 435/6.16 |
| 2011/0027190 A1* | 2/2011 | Hasmann | A61K 39/39558 424/9.6 |
| 2011/0030074 A1* | 2/2011 | Depinho | A01K 67/0276 800/10 |
| 2011/0074944 A1* | 3/2011 | Can | G06T 5/50 348/79 |
| 2013/0044933 A1 | 2/2013 | Kenny | |
| 2013/0165330 A1 | 6/2013 | Natarajan et al. | |

FOREIGN PATENT DOCUMENTS

| | | |
|---|---|---|
| JP | 2004-532410 A | 10/2004 |
| JP | 2010-500571 A | 1/2010 |
| JP | 2010-510492 A | 4/2010 |
| JP | 2012-503180 A | 2/2012 |
| WO | 2008/021677 | 2/2008 |
| WO | 2008/023055 A1 | 2/2008 |
| WO | 2008021677 A2 | 2/2008 |
| WO | 2008064067 A2 | 5/2008 |
| WO | 2008/133729 | 11/2008 |
| WO | 2010/005991 | 1/2010 |
| WO | 2011/040872 | 4/2011 |

OTHER PUBLICATIONS

"List of sequenced bacterial genomes" (Wikipedia.com; accessed Jan. 24, 2014).*

"Custom Antibody Services" (PrecisionAntibody.com; accessed Mar. 4, 2014).*

Ponomarenko et al., "The Size of the Human Proteome: The Width and Depth," International Journal of Analytical Chemistry, 2016, 6 pages.*

Ko, "Hominin interbreeding and the evolution of human variation," Journal of Biological Research—Thessaloniki, 2016.*

Michael F. Hammer "Human Hybrids", Scientific American, May 2013, pp. 66-71. (Year: 2013).*

Teixeira and Cooper, "Using hominin introgression to trace modern human dispersals", PNAS, Jul. 30, 2019, vol. 116, No. 31, pp. 15327-15332. (Year: 2019).*

Gaiser et al., "Automated analysis of protein expression and gene amplification within he same cells of paraffin-embedded tumour tissue", Analytical Cellular Pathology/Cellular Oncology, 33(2010) 105-112. (Year: 2010).*

Ha, et.al. Cancer Research, vol. 72, No. 24, Suppl. 3, Dec. 15, 2012 pp. 3-5.

Gaiser, Analytical Cellular Pathology/Cellular Oncology vol. 33, Jan. 1, 2010 pp. 105-112.

GE, Journal of Histochemistry & Cytochemistry, vol. 54, No. 7, Mar. 3, 3006 pp. 843-847.

Fiegl, et.al. Cytometry, vol. 38, No. 1, Feb. 15, 1999, pp. 15-23.

PCT/US2013/033286 ISRWO Dated Sep. 16, 2013.

Birgitta Schla 1/4 Ter et al., "Combined detection of Her2/neu gene amplification and protein overexpression in effusions from patients with breast and ovarian cancer," Journal of Cancer Research and Clinical Oncology, Springer, Berlin, DE, vol. 136, No. 9, Mar. 9, 2010, pp. 1389-1400, XP019849089, ISSN: 1432-1335.

A Vincent-Salomon et al., "Calibration of immunohistochemistry for assessment of HER2 in breast cancer: results of the French Multicentre GEFRPICS Study", Histopathology, vol. 42, No. 4, Apr. 1, 2003, pp. 337-347.

A Seppo et al., "Automated analysis of HER2 Fish using combined immunofluorescence and FISH signals," Dec. 4, 2012, retrieved from the internet: URL: http://www.multiomyx.com/wp-content/uploads/2014/12/JB26529US_Automated-analysis-of-Her2-FISH-using-combined-immunofluorescence-and-FISH-signals.pdf, 1 page.

Lottner., C., et al., "Simultaneous detection of HER2/neu gene amplification and protein overexpression in paraffin-embedded breast cancer," The Journal of Pathology, vol. 205, Issue 5, pp. 1-3 (Apr. 2005) (Abstract).

Reisenbichler., E.S., et al., "Evaluation of Dual Immunohistochemistry and Chromogenic In Situ Hybridization for ER2 on a Single Section," American Journal of Clinical Pathology, vol. 137, Issue 1, pp. 102-110 (Jan. 2012).

Written Opinion issued in connection with corresponding SG Application No. 11201406104Q dated Feb. 17, 2016.

Notification of Reason for Refusal issued in connection with corresponding JP Application No. 2015-503398 dated Sep. 12, 2017.

* cited by examiner

METHODS FOR GENERATING AN IMAGE OF A BIOLOGICAL SAMPLE

This application is a filing under 35 U.S.C. 371of international application number PCT/US2013/033286, filed Mar. 21, 2013, which claims priority to U.S. application No. 61/618,282 filed Mar. 30, 3012, the entire disclosure of which is hereby incorporated by reference.

FIELD OF THE INVENTION

The present invention is directed to methods for generating an image of a biological sample. More specifically, the present invention is directed to a method for generating two or more images of the same biological sample, each after subjecting the sample to a reaction protocol. Also provided are a kit and a system for performing the novel methods.

BACKGROUND OF THE INVENTION

Most diseases have a heterogeneous phenotype, and require complex characterization for patient assessment. Breast cancer, for example, consists of five distinct subtypes, with each subtype associated with different phenotypes, survival times, and therapy responsiveness. For example, luminal types have the best prognosis and respond well to hormonal therapies, whereas patients with HER2-positive and basal tumors fare poorly. While recent developments of targeted therapies have made significant impacts in the treatment of HER2-positive tumors, many of these patients fail to respond, or develop resistance. In many of these cases, mutations in the HER2 gene or the activation of other pathways, (e.g. PI3K/AKT) have been identified, and new therapies that target both normal and mutated-HER2 or combination therapies that also affect these other pathways have been suggested. Additionally, several studies have even indicated that changes in the same gene in different breast cancer subtypes may impact both the course of disease and therapy response differently. Thus, comprehensive profiling of a patient's tumor is of the utmost importance for a physician to be able to make the best treatment decision for that patient.

In a fraction of patients with breast cancer, the HER2 gene is amplified as part of the process of malignant transformation and tumor progression. HER2 gene amplification generally leads to overexpression of the HER2 protein on the surface of breast cancer cells. Amplification of the HER2 gene and/or overexpression of its protein have been demonstrated in 25-30% of breast cancers. Several studies have shown that HER2 status correlates with sensitivity or resistance to certain chemotherapy regimens. Demonstration of high HER2 protein overexpression or HER2 gene amplification is essential for initiating therapy with Herceptin™, a monoclonal antibody to HER2 protein. Clinical studies have shown that patients whose tumors have high HER2 protein overexpression and/or amplification of the HER2 gene benefit most from Herceptin™. There is a recommendation that both HER2 protein level and HER2 gene amplification should be measured. However, two patient samples are routinely used to conduct the IHC and FISH analysis, potentially resulting in a lack of concordance between the two results. Ideally both analyses would be conducted on the same sample and at a cell to cell level.

In patients with advanced or metastatic cancer of the stomach or gastro-esophageal junction, approximately 20% have a HER2-positive disease. Adenocarcinomas are more commonly HER2-positive than undifferentiated carcinomas and mixed tumors; cancers of the gastro-esophageal junction are more likely to be HER2-positive than the tumors of the stomach. Trastuzumab™ has been shown to improve survival of patients with HER2-positive advance or metastatic cancer of the stomach or gastro-esophageal junction. Studies demonstrated that gene amplification (FISH) and protein overexpression (using immunofluorescence detection) are not as correlated as with breast cancer, therefore a single method should not be used to determine HER-2 status.

Although various methods may be used in biology and in medicine to observe different targets in a biological sample, many of the current techniques may detect only a few targets at one time (such as, immunofluorescence (IF) where number of targets detectable is limited by the florescence-based detection system) in a single sample. Further analysis of targets may require use of additional biological samples from the source limiting the ability to determine relative characteristics of the targets such as the presence, absence, concentration, and/or the spatial distribution of multiple biological targets in the biological sample. Moreover, in certain instances, a limited amount of sample may be available for analysis or the individual sample may require further analysis for other proteins of interest such as cell cycle or other cancer biomarkers. Thus, methods, agents, and devices capable of iteratively analyzing an individual sample are needed.

Several laboratories have attempted to combine protein expression and DNA based analysis on a single sample. Lottner et al. described a protocol which performs FISH first, then perform IF of HER2 on a single tissue sample, followed by image analysis. *J Pathol.* 2005; 205(5):577-84; doi: 10.1002/path.1742. The authors noted that performing IF prior to FISH results in higher background fluorescence and weaker immunofluorescence. Reisenbichler et al. experimented on the combination of immunohistochemistry (IHC) and chromogenic in situ hybridization (CISH) for HER2 on a single sample. Am J Clin Pathol 2012; 137:102-110; doi: 10.1309/AJCPLNHINN9O6YSF. While the authors were able to obtain signal by first imaging CISH sample, followed by imaging IHC sample, they found that better images were obtained when not only IHC is performed after CISH, also the sample was only imaged until the completion of all wet lab experimentation (i.e. without an intermediate imaging step). Importantly, Reisenbichler et al. could not obtain CISH signal when they first performed IHC on the sample, then performed CISH.

Gaiser et al. described a method for the analysis of tissue structures localized by protein expression for gene amplification within the same tissue sample. The authors first detected CD133 expression in colon cancer tissue samples, using monoclonal antibody and FITC-labeled secondary antibody. Using 40× magnification, regions of interest were manually selected and recorded. After imaging, FISH analysis was performed simultaneously for amplified cMyc oncogene and ZNF217. The sample was again imaged in the same regions at 40× magnification. An automated microscope and custom designed classifier for tile based FISH analysis was used to analyze the images. Anal Cell Pathol (Amst). 2010; 33(2): 105-112; doi: 10.3233/ACP-CLO-2010-0532).

There is still a need for improved methods for the detection of multiple targets in the same biological sample and the creation of a composite image to compare expression on a cell by cell basis, allowing the inclusion or exclusion of cells based on protein expression, apoptosis etc.

SUMMARY OF THE INVENTION

In one aspect of the invention, it is provided a method for the generation of an image of a region of interest in a biological sample comprising the steps of (1) generating a first image including the region of interest of the biological sample having undergone a first protocol but not a second protocol; and (2) generating a second image including the region of interest of the biological sample after having undergone a second protocol; wherein the region of interest is smaller than the sample. In some embodiments, the region of interest is selected by comparing the first image of the biological sample to pre-determined criterion. In certain embodiments, the first protocol includes immonufluorescence detection of a target protein. In certain embodiments, the second protocol includes fluorescence detection of at least one target nucleic acid sequence by hybridizing a probe with the target nucleic acid sequence. In other embodiments, the second protocol includes immonufluorescence detection of a different target protein. In certain embodiments, the method further comprises generating a composite image that includes at least the regions of interest from each of the first and the second images. In some embodiments, the composite image is generated by a method which comprises registering locations of selected signals obtained during the generation of the first image with locations of selected signals obtained during the generation of the second image. In certain embodiments, the locations of selected signals are from within the region of interest.

In certain embodiments, the first or the second protocol comprises staining the sample with a fluorescent marker that provides morphological information.

In certain embodiments, the first or the second protocol comprises detecting autofluorescense of the biological sample.

In certain embodiments, the first and second images are fluorescent images.

In certain embodiments, the second image covers a smaller area of the biological sample compared to the area covered by the first image.

In another aspect of the invention, it is provided a method of generating an image of a biological sample, comprising the steps of: (1) generating a first image of the biological sample after a first protocol and before a second protocol is performed on the biological sample; and (2) imaging a region of interest of the sample after the second protocol has been performed on the region of interest of the biological sample, the region of interest being smaller than said sample.

In another aspect of the invention, it is provided a method of imaging a biological sample, comprising the steps of (1) generating a first image of the biological sample after performing a first protocol but prior to performing a second protocol thereon; and generating a second image of a region of interest of the sample after performing the second protocol on the region of interest, wherein the region of interest is smaller than the sample.

In another aspect of the invention, it is provided a method of analyzing a biological sample, comprising providing a composite image of the biological sample, and analyzing the expression of the protein and the nucleic acid sequences of interest from the composite image.

In still another aspect of the invention, it is provided a kit for the fluorescent detection of a protein as well as a target nucleic acid sequence on the same biological sample. Thus, an embodiment of the invention provides a kit that includes components for performing the novel method of the invention.

In yet another aspect of the invention, it is provided a system for the fluorescent detection of a protein as well as a target nucleic acid sequence on the same biological sample. Thus, one embodiment of the invention provides a system that includes means for performing the novel method of the invention.

DETAILED DESCRIPTION OF THE INVENTION

Figure 1:
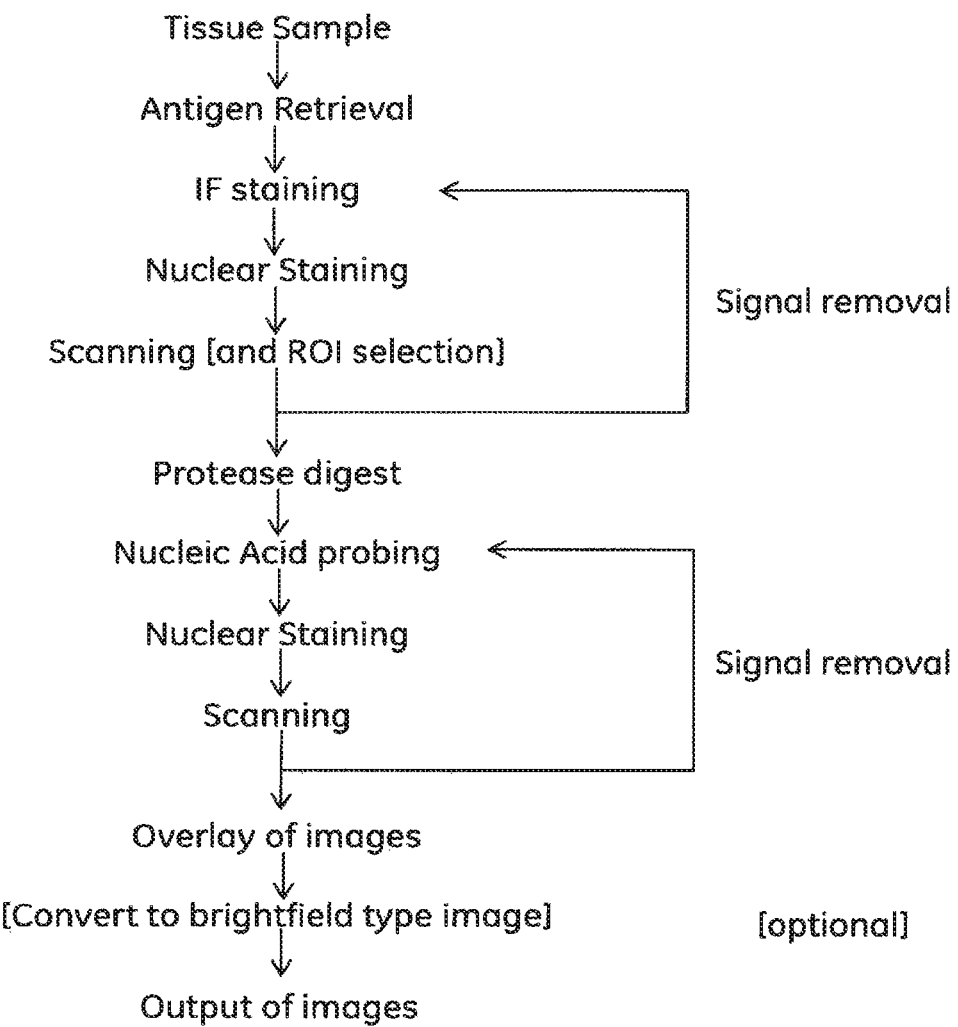
FIG. 1 is a flowchart showing the key steps for an embodiment of the invention.

Definitions:

To more clearly and concisely describe and point out the subject matter of the claimed invention, the following definitions are provided for specific terms that are used in the following description and the claims appended hereto.

The singular forms "a" "an" and "the" include plural referents unless the context clearly dictates otherwise. Approximating language, as used herein throughout the specification and claims, may be applied to modify any quantitative representation that could permissibly vary without resulting in a change in the basic function to which it is related. Accordingly, a value modified by a term such as "about" is not to be limited to the precise value specified. Unless otherwise indicated, all numbers expressing quantities of ingredients, properties such as molecular weight, reaction conditions, so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the embodiments of the present invention. At the very least each numerical parameter should at least be construed in light of the number of reported significant digits and by applying ordinary rounding techniques.

As used herein, the term "solid support" refers to an article on which the biological sample may be immobilized and the protein and target nucleic acid sequence may be subsequently detected by the methods disclosed herein. The biological sample may be immobilized on the solid support by physical adsorption, by covalent bond formation, or by combinations thereof. A solid support may include a polymeric, a glass, or a metallic material. Examples of solid supports include a membrane, a microtiter plate, a bead, a filter, a test strip, a slide, a cover slip, and a test tube.

As used herein, the term "fluorescent marker" refers to a fluorophore that selectively stains particular subcellular compartments. Examples of suitable fluorescent marker (and their target cells, subcellular compartments, or cellular components if applicable) may include, but are not limited to: 4',6-diamidino-2-phenylindole (DAPI) (nucleic acids), Eosin (alkaline cellular components, cytoplasm), Hoechst 33258 and Hoechst 33342 (two bisbenzimides) (nucleic acids), Propidium Iodide (nucleic acids), Quinacrine (nucleic acids), Fluorescein-phalloidin (actin fibers), Chromomycin A 3 (nucleic acids), Acriflavine-Feulgen reaction (nucleic acid), Auramine O-Feulgen reaction (nucleic acids), Ethidium Bromide (nucleic acids). Nissl stains (neurons), high affinity DNA fluorophores such as POPO, BOBO, YOYO and TOTO and others, and Green Fluorescent Protein fused to DNA binding protein (e.g., histones), ACMA, and Acridine Orange. Preferably, the fluorescent marker stains the nucleus.

As used herein, the term "fluorophore" refers to a chemical compound, which when excited by exposure to a particular wavelength of light, emits light (at a different wavelength). The terms "fluorescence", "fluorescent", or "fluorescent signal" all refer to the emission of light by an excited fluorophore. Fluorophores may be described in terms of their emission profile, or "color." Green fluorophores (for example Cy3, FITC, and Oregon Green) may be characterized by their emission at wavelengths generally in the range of 515-540 nanometers. Red fluorophores (for example Texas Red, Cy5, and tetramethylrhodamine) may be characterized by their emission at wavelengths generally in the range of 590-690 nanometers. Examples of fluorophores include, but are not limited to, 4-acetamido-4'-isothiocyanatostilbene-2,2'disulfonic acid, acridine, derivatives of acridine and acridine isothiocyanate, 5-(2'-aminoethyl) aminonaphthalene-1-sulfonic acid (EDANS), 4-amino-N-[3-vinylsulfonyl)phenyl]naphthalimide-3,5 disulfonate (Lucifer Yellow VS), N-(4-anilino-1-naphthyl)maleimide, anthranilamide, Brilliant Yellow, coumarin, coumarin derivatives, 7-amino-4-methylcoumarin (AMC, Coumarin 120), 7-amino-trifluoromethylcouluarin (Coumaran 151), cyanosine; 4',6-diaminidino-2-phenylindole (DAPI), 5',5"-dibromopyrogallol-sulfonephthalein (Bromopyrogallol Red), 7-diethylamino-3-(4'-isothiocyanatophenyl)4-methylcoumarin, 4,4'-diisothiocyanatodihydro-stilbene-2,2'-disulfonic acid, 4,4'-diisothiocyanatostilbene-2,2'-disulfonic acid, 5-[dimethylamino]naphthalene-1-sulfonyl chloride (DNS, dansyl chloride), eosin, derivatives of eosin such as eosin isothiocyanate, erythrosine, derivatives of erythrosine such as erythrosine B and erythrosin isothiocyanate; ethidium; fluorescein and derivatives such as 5-carboxyfluorescein (FAM), 5-(4,6-dichlorotriazin-2-yl) aminofluorescein (DTAF), 2'7'-dimethoxy-4'5'-dichloro-6-carboxyfluorescein (JOE), fluorescein, fluorescein isothiocyanate (FITC), QFITC (XRITC); fluorescamine derivative (fluorescent upon reaction with amines); IR144; IR1446; Malachite Green isothiocyanate; 4-methylumbelliferone; ortho cresolphthalein; nitrotyrosine; pararosaniline; Phenol Red, B-phycoerythrin; o-phthaldialdehyde derivative (fluorescent upon reaction with amines); pyrene and derivatives such as pyrene, pyrene butyrate and succinimidyl 1-pyrene butyrate; Reactive Red 4 (Cibacron® Brilliant Red 3B-A), rhodamine and derivatives such as 6-carboxy-X-rhodamine (ROX), 6-carboxyrhodamine (R6G), lissamine rhodamine B sulfonyl chloride, rhodamine (Rhod), rhodamine B, rhodamine 123, rhodamine X isothiocyanate, sulforhodamine B, sulforhodamine 101 and sulfonyl chloride derivative of sulforhodamine 101 (Texas Red); N,N,N',N'-tetramethyl-6-carboxyrhodamine (TAMRA); tetramethyl Rhodamine, tetramethyl rhodamine isothiocyanate (TRITC); riboflavin; rosolic acid and lathanide chelate derivatives, quantum dots, cyanines, and squaraines. In some embodiments, a fluorophore may essentially include a fluorophore that may be attached to an antibody, for example, in an immunofluorescence analysis. Suitable fluorophores that may be conjugated to a antibody include, but are not limited to, Fluorescein, Rhodamine, Texas Red, Cy2, Cy3, Cy5, VECTOR Red, ELF™ (Enzyme-Labeled Fluorescence), Cy2, Cy3, Cy3.5, Cy5, Cy7, FluorX, Calcein, Calcein-AM, CRYPTOFLUOR™'S, Orange (42 kDa), Tangerine (35 kDa), Gold (31 kDa), Red (42 kDa), Crimson (40 kDa), BHMP, BHDMAP, Br-Oregon, Lucifer Yellow, Alexa dye family, N-[6-(7-nitrobenz-2-oxa-1,3-diazol-4-yl)amino]caproyl] (NBD), BODIPY, boron dipyrromethene difluoride, Oregon Green, MITOTRACKER, Red, DiOC.sub.7 (3), DiIC.sub.18, Phycoerythrin, Phycobiliproteins BPE (240 kDa) RPE (240 kDa) CPC (264 kDa) APC (104 kDa), Spectrum Blue, Spectrum Aqua, Spectrum Green, Spectrum Gold, Spectrum Orange, Spectrum Red, NADH, NADPH, FAD, Infra-Red (IR) Dyes, Cyclic GDP-Ribose (cGDPR), Calcofluor White, Lissamine, Umbelliferone, Tyrosine or Tryptophan. In some embodiments, a fluorophore may essentially include a cyanine dye. In some embodiments, a fluorophore may essentially include one or more cyanine dye (e.g., Cy3 dye, a Cy5 dye, or a Cy7 dye).

As used herein, the term "antibody" refers to an immunoglobulin that specifically binds to and is thereby defined as complementary with a particular spatial and polar organization of another molecule. The antibody may be monoclonal or polyclonal and may be prepared by techniques that are well known in the art such as immunization of a host and collection of sera (polyclonal), or by preparing continuous hybrid cell lines and collecting the secreted protein (monoclonal), or by cloning and expressing nucleotide sequences or mutagenized versions thereof, coding at least for the amino acid sequences required for specific binding of natural antibodies. Antibodies may include a complete immunoglobulin or fragment thereof, which immunoglobulins include the various classes and isotypes, such as IgA, IgD, IgE, IgG1, IgG2a, IgG2b and IgG3, IgM. Functional antibody fragments may include portions of an antibody capable of retaining binding at similar affinity to full-length antibody (for example, Fab, Fv and F(ab')2, or Fab'). In addition, aggregates, polymers, and conjugates of immunoglobulins or their fragments may be used where appropriate so long as binding affinity for a particular molecule is substantially maintained.

"Target," as used herein, generally refers to the component of a biological sample that may be detected when present in the biological sample. The target may be any substance for which there exists a naturally occurring specific binder (e.g., an antibody), or for which a specific binder may be prepared (e.g., a small molecule binder). In general, the binder may bind to target through one or more discrete chemical moieties of the target or a three-dimensional structural component of the target (e.g., 3D structures resulting from peptide folding). The target may include one or more of peptides, proteins (e.g., antibodies, affibodies, or aptamers), nucleic acids (e.g., polynucleotides, DNA, RNA, or aptamers); polysaccharides (e.g., lectins or sugars), lipids, enzymes, enzyme substrates, ligands, receptors, antigens, or haptens. In some embodiments, targets may include proteins or nucleic acids.

As used herein, the term "binder" refers to a biological molecule that may bind to one or more targets in the biological sample. A binder may specifically bind to a target. Suitable binders may include one or more of natural or modified peptides, proteins (e.g., antibodies, affibodies, or aptamers), nucleic acids (e.g., polynucleotides, DNA, RNA, or aptamers); polysaccharides (e.g., lectins, sugars), lipids, enzymes, enzyme substrates or inhibitors, ligands, receptors, antigens, haptens, and the like. A suitable binder may be selected depending on the sample to be analyzed and the targets available for detection. For example, a target in the sample may include a ligand and the binder may include a receptor or a target may include a receptor and the probe may include a ligand. Similarly, a target may include an antigen and the binder may include an antibody or antibody fragment or vice versa. In some embodiments, a target may include a nucleic acid and the binder may include a complementary nucleic acid. In some embodiments, both the target and the binder may include proteins capable of binding to each other.

As used herein, the term "specific binding" refers to the specific recognition of one of two different molecules for the other compared to substantially less recognition of other molecules. The molecules may have areas on their surfaces or in cavities giving rise to specific recognition between the two molecules arising from one or more of electrostatic interactions, hydrogen bonding, or hydrophobic interactions. Specific binding examples include, but are not limited to, antibody-antigen interactions, enzyme-substrate interactions, polynucleotide interactions, and the like. In some embodiments, a binder molecule may have an intrinsic equilibrium association constant (KA) for the target no lower than about $10^5$ $M^{-1}$ under ambient conditions (i.e., a pH of about 6 to about 8 and temperature ranging from about 0° C. to about 37° C.).

As used herein, the term "in situ" generally refers to an event occurring in the original location, for example, in intact organ or tissue or in a representative segment of an organ or tissue. In some embodiments, in situ analysis of targets may be performed on cells derived from a variety of sources, including an organism, an organ, tissue sample, or a cell culture. In situ analysis provides contextual information that may be lost when the target is removed from its site of origin. Accordingly, in situ analysis of targets describes analysis of target-bound probe located within a whole cell or a tissue sample, whether the cell membrane is fully intact or partially intact where target-bound probe remains within the cell. Furthermore, the methods disclosed herein may be employed to analyze targets in situ in cell or tissue samples that are fixed or unfixed.

A "chemical agent" may include one or more chemicals capable of modifying the fluorophore or the cleavable linker (if present) between the fluorophore and the binder. A chemical agent may be contacted with the fluorophore in the form of a solid, a solution, a gel, or a suspension. Suitable chemical agents useful to modify the signal include agents that modify pH (for example, acids or bases), electron donors (e.g., nucleophiles), electron acceptors (e.g., electrophiles), oxidizing agents, reducing agents, or combinations thereof. In some embodiments, a chemical agent may include a base, for example, sodium hydroxide, ammonium hydroxide, potassium carbonate, or sodium acetate. In some embodiments, a chemical agent may include an acid, for example, hydrochloric acid, sulfuric acid, acetic acid, formic acid, trifluoroacetic acid, or dichloroacetic acid. In some embodiments, a chemical agent may include nucleophiles, for example, cyanides, phosphines, or thiols. In some embodiments, a chemical agent may include reducing agents, for example, phosphines, thiols, sodium dithionite, or hydrides that can be used in the presence of water such as borohydride or cyanoborohydrides. In some embodiments, a chemical agent may include oxidizing agents, for example, active oxygen species, hydroxyl radicals, singlet oxygen, hydrogen peroxide, or ozone. In some embodiments, a chemical agent may include a fluoride, for example tetrabutylammonium fluoride, pyridine-HF, or $SiF_4$.

One or more of the aforementioned chemical agents may be used in the methods disclosed herein depending upon the susceptibility of the fluorophore, of the binder, of the target, or of the biological sample to the chemical agent. In some embodiments, a chemical agent that essentially does not affect the integrity of the binder, the target, and the biological sample may be employed. In some embodiments, a chemical agent that does not affect the specificity of binding between the binder and the target may be employed.

In some embodiments, where two or more fluorophores may be employed simultaneously, a chemical agent may be capable of selectively modifying one or more signal generators. Susceptibility of different signal generators to a chemical agent may depend, in part, to the concentration of the signal generator, temperature, or pH. For example, two different fluorophores may have different susceptibility to a base depending upon the concentration of the base.

As used herein the term "brightfield type image" or "virtual stained image" (VSI) refers to an image of a biological sample that simulates that of an image obtained from a brightfield staining protocol. The image has similar contrast, intensity, and coloring as a brightfield image. This allows features within a biological sample, including but not limited to nuclei, epithelia, stroma or any type of extracellular matrix material features, to be characterized as if the brightfield staining protocol was used directly on the biological sample.

General Description of the Invention

The invention includes embodiments that relate generally to methods applicable in analytical, diagnostic, or prognostic applications which combine immunofluorescence detection with fluorescence based nucleic acid analysis. The disclosed methods relate generally to detection and correlation of different kinds of targets (i.e., protein and nucleic acid) from a single biological sample. In some embodiments, methods of detecting multiple targets of the same kind (i.e., protein or nucleic acid, respectively) using the same detection channel are disclosed. In such embodiments, correlations can be drawn among the multiple, different kinds of targets.

The methods disclosed herein may allow detection of a plurality of targets in the same biological sample with little or no effect on the integrity of the biological sample. Detecting the targets in the same biological sample may further provide relative, spatial information about the targets in the biological sample. Methods disclosed herein may also be applicable in analytical applications where a limited amount of biological sample may be available for analysis and the same sample may have to be processed for multiple analyses. Furthermore, the same detection channel may be employed for detection of different targets in the sample, enabling fewer chemistry requirements for analyses of multiple targets. The methods may further facilitate analyses based on detection methods that may be limited in the number of simultaneously detectable targets because of limitations of resolvable signals.

In some embodiments, the method of detecting multiple targets in a biological sample includes sequential detection of targets in the biological sample. The method generally includes the steps of detecting a first target in the biological sample, optionally modifying the signal from the first target, and detecting a second target in the biological sample. The method may further include repeating the step of modification of signal from the first or second target followed by detecting a different target in the biological sample, and so forth.

Thus, in one aspect of the invention, it is provided a method for the generation of an image of a region of interest in a biological sample comprising the steps of (1) generating a first image including the region of interest of the biological sample having undergone a first protocol but not a second protocol; and (2) generating a second image including the region of interest of the biological sample after having undergone a second protocol; wherein the region of interest is smaller than the sample. In some embodiments, the region of interest is selected by comparing the first image of the biological sample to pre-determined criterion. In certain embodiments, the first protocol includes immunufluorescence detection of a target protein. In certain embodiments, the second protocol includes fluorescence detection of at least one target nucleic acid sequence by hybridizing a probe with the target nucleic acid sequence. In other embodiments, the second protocol includes immonufluorescence detection of a different target protein. In certain embodiments, the method further comprises generating a composite image that includes at least the regions of interest from each of the first and the second images. In some embodiments, the composite image is generated by a method which comprises registering locations of selected signals obtained during the generation of the first image with locations of selected signals obtained during the generation of the second image. In certain embodiments, the locations of selected signals are from within the region of interest.

In certain embodiments, the first or the second protocol comprises staining the sample with a fluorescent marker that provides morphological information.

In certain embodiments, the first or the second protocol comprises detecting autofluorescense of the biological sample.

In certain embodiments, the first and second images are fluorescent images.

In another aspect of the invention, it is provided a method of generating an image of a biological sample, comprising the steps of: (1) generating a first image of the biological sample after a first protocol and before a second protocol is performed on the biological sample; and (2) imaging a region of interest of the sample after the second protocol has been performed on the region of interest of the biological sample, the region of interest being smaller than said sample. Preferably, step (2) includes the generation of a second image.

In another aspect of the invention, it is provided a method of imaging a biological sample, comprising the steps of (1) generating a first image of the biological sample after performing a first protocol but prior to performing a second protocol thereon; and (2) generating a second image of a region of interest of the sample after performing the second protocol on the region of interest, wherein the region of interest is smaller than the sample.

In certain embodiment, the method for generating the first image includes the steps of: (a) contacting the sample on a solid support with a first binder for a target protein; (b) staining the sample with a fluorescent marker that provides morphological information; (c) detecting, by fluorescence, signals from the first binder and the fluorescent marker; (d) generating the first image of at least part of the sample from the detected fluorescent signals.

In certain embodiment, the method for generating the second image of the biological sample comprising the steps of: (a) contacting the same sample with a probe for each of at least one target nucleic acid sequence thus hybridizing the probes with the target nucleic acid sequence; (b) optionally, staining the sample with the fluorescent marker; (c) detecting, by fluorescence, signals from the probes for each of the target nucleic acid sequences and the fluorescent marker; and (d) generating the second image of at least part of the sample from the detected fluorescent signal.

In other embodiment, the method for generating the second image of the biological sample comprising the steps of: (a) contacting the sample on a solid support with a second binder for a different target protein; (b) optionally, staining the sample with the fluorescent marker; (c) detecting, by fluorescence, signals from the second binder and the fluorescent marker; (d) generating the second image of at least part of the sample from the detected fluorescent signals.

In certain embodiments, the methods further includes generating a composite image comprises using signal information acquired in the generation of the first image and the generation of the second image to generate the composite image. In certain embodiments, the step of generating the composite image comprises registering the location of signals from the fluorescent marker acquired in the first image with the location of signals from the fluorescent marker acquired in the second image.

In certain embodiments, the step (d) generating the first image of at least part of the sample from the detected fluorescent signals comprises: (i) generating an initial image of at least part of the sample from the detected fluorescent signals; and (ii) selecting a region of interest from the initial image, and detecting by fluorescence, signals from at least the first binder and the fluorescent marker to generate the first image at a higher resolution than the initial image. In certain embodiments, the composite image is generated by combining signal information from the higher resolution image and the second image. In other embodiments, the composite image is generated by a method comprising registering the location of signals from the fluorescent marker in the higher resolution image with the location of signals from the fluorescent marker in the second image. In still other embodiments, the generation of the composite image comprises registering the location of signals from the fluorescent marker acquired in the first image with the location of signals from the fluorescent marker acquired in the second image.

In a specific embodiment, the method comprises generating a first low magnification image of a formalin fixed, paraffin embedded tissue sample which has been stained by immunofluorescence for one or more markers and fluorescent marker (e.g., DAPI) staining; generating a virtual H&E or virtual DAB image from the low magnification image and using that to select regions of interest based on staining intensity or morphology; generating a second image of the sample which has been stained by FISH and fluorescent marker staining; overlaying or registering the images based on common images obtained using the fluorescent marker staining as co-ordinates to generate a composite image. In certain embodiments, the method further comprises analyzing the images to measure for protein expression and the amount of target nucleic acid sequences in individual cells.

Biological Samples

A biological sample in accordance with one embodiment of the invention may be solid or fluid. Biological sample refers to a sample obtained from a biological subject, including sample of biological tissue or fluid origin obtained in vivo or in vitro. Suitable examples of biological samples may include, but are not limited to, blood, saliva, cerebral spinal fluid, pleural fluid, milk, lymph, sputum, semen, urine, stool, tears, needle aspirates, external sections of the skin, respiratory, intestinal, and genitourinary tracts, tumors, organs, cell cultures, or solid tissue sections. In some embodiments, the biological sample may be analyzed as is, that is, without harvest and/or isolation of the target of interest. In an alternate embodiment, harvest of the sample may be performed prior to analysis. In some embodiments, the methods disclosed herein may be particularly suitable for in-vitro analysis of biological samples. Biological samples may be immobilized on a solid support, such as in glass slides, microtiter, or ELISA plates.

A biological sample may include any of the aforementioned samples regardless of their physical condition, such as, but not limited to, being frozen or stained or otherwise treated. In some embodiments, a biological sample may include compounds which are not naturally intermixed with the sample in nature such as preservatives, anticoagulants, buffers, fixatives, nutrients, antibiotics, or the like.

A biological sample may be of prokaryotic origin or eukaryotic origin (e.g., insects, protozoa, birds, fish, reptiles). In some embodiments, the biological sample is mammalian (e.g., rat, mouse, cow, dog, donkey, guinea pig, or rabbit). In certain embodiments, the biological sample is of primate origin (e.g., example, chimpanzee or human).

In some embodiments, a biological sample may include a tissue sample, a whole cell, a cell constituent, a cytospin, or a cell smear. In some embodiments, a biological sample essentially includes a tissue sample. A tissue sample may include a collection of similar cells obtained from a tissue of a biological subject that may have a similar function. In some embodiments, a tissue sample may include a collection of similar cells obtained from a tissue of a human. Suitable examples of human tissues include, but are not limited to, (1) epithelium; (2) the connective tissues, including blood vessels, bone and cartilage; (3) muscle tissue; and (4) nerve tissue. The source of the tissue sample may be solid tissue obtained from a fresh, frozen and/or preserved organ or tissue sample or biopsy or aspirate; blood or any blood constituents; bodily fluids such as cerebral spinal fluid, amniotic fluid, peritoneal fluid, or interstitial fluid; or cells from any time in gestation or development of the subject. In some embodiments, the tissue sample may include primary or cultured cells or cell lines.

The tissue sample may be obtained by a variety of procedures including, but not limited to surgical excision, aspiration or biopsy. In some embodiments, the tissue sample may be fixed and embedded in paraffin. The tissue sample may be fixed or otherwise preserved by conventional methodology; the choice of a fixative may be determined by the purpose for which the tissue is to be histologically stained or otherwise analyzed. The length of fixation may depend upon the size of the tissue sample and the fixative used. For example, neutral buffered formalin, Bouin's or paraformaldehyde, may be used to fix or preserve a tissue sample.

In some embodiments, a biological sample includes tissue sections of normal or cancerous origin, such as tissue sections form colon, breast, prostate, lung, liver, and stomach. A tissue section may include a single part or piece of a tissue sample, for example, a thin slice of tissue or cells cut from a tissue sample. In some embodiments, multiple sections of tissue samples may be taken and subjected to analysis, provided the methods disclosed herein may be used for analysis of the same section of the tissue sample with respect to at least two different targets (i.e., one of these being of a protein origin and another one being a nucleic acid origin). A tissue section, if employed as a biological sample may have a thickness in a range that is less than about 100 micrometers, in a range that is less than about 50 micrometers, in a range that is less than about 25 micrometers, or in range that is less than about 10 micrometers.

Target Proteins

A target protein according to an embodiment of the invention may be present on the surface of a biological sample (for example, an antigen on a surface of a tissue section) or present in the bulk of the sample (for example, an antibody in a buffer solution). In some embodiments, a target protein may not be inherently present on the surface of a biological sample and the biological sample may have to be processed to make the target protein available on the surface. In some embodiments, the target protein may be in a tissue, either on a cell surface, or within a cell.

Suitability of target protein to be analyzed may be determined by the type and nature of analysis required for the biological sample. In some embodiments, a target may provide information about the presence or absence of an analyte in the biological sample. In another embodiment, a target protein may provide information on a state of a biological sample. For example, if the biological sample includes a tissue sample, the methods disclosed herein may be used to detect target protein that may help in comparing different types of cells or tissues, comparing different developmental stages, detecting the presence of a disease or abnormality, or determining the type of disease or abnormality.

Suitable target proteins may include one or more of peptides, proteins (e.g., antibodies, affibodies, or aptamers), enzymes, ligands, receptors, antigens, or haptens. One or more of the aforementioned target proteins may be characteristic of particular cells, while other target proteins may be associated with a particular disease or condition. In some embodiments, target proteins in a tissue sample that may be detected and analyzed using the methods disclosed herein may include, but are not limited to, prognostic markers, predictive markers, hormone or hormone receptors, lymphoids, tumor markers, cell cycle associated markers, neural tissue and tumor markers, or cluster differentiation markers.

Suitable examples of prognostic markers may include enzymatic targets such as galactosyl transferase II, neuron specific enolase, proton ATPase-2, or acid phosphatase. Other examples of prognostic protein or gene markers include Ki67, cyclin E, p53, cMet.

Suitable examples of predictive markers (drug response) may include protein or gene targets such as EGFR, Her2, ALK.

Suitable examples of hormone or hormone receptors may include human chorionic gonadotropin (HCG), adrenocorticotropic hormone, carcinoembryonic antigen (CEA), prostate-specific antigen (PSA), estrogen receptor, progesterone receptor, androgen receptor, gC1q-R/p33 complement receptor, IL-2 receptor, p75 neurotrophin receptor, PTH receptor, thyroid hormone receptor, or insulin receptor.

Suitable examples of lymphoids may include alpha-1-antichymotrypsin, alpha-1-antitrypsin, B cell target, bcl-2, bcl-6, B lymphocyte antigen 36 kD, BM1 (myeloid target), BM2 (myeloid target), galectin-3, granzyme B, HLA class I Antigen, HLA class II (DP) antigen, HLA class II (DQ) antigen, HLA class II (DR) antigen, human neutrophil defensins, immunoglobulin A, immunoglobulin D, immunoglobulin G, immunoglobulin M, kappa light chain, kappa light chain, lambda light chain, lymphocyte/histocyte antigen, macrophage target, muramidase (lysozyme), p80 anaplastic lymphoma kinase, plasma cell target, secretory leukocyte protease inhibitor, T cell antigen receptor (JOVI 1), T cell antigen receptor (JOVI 3), terminal deoxynucleotidyl transferase, or unclustered B cell target.

Suitable examples of tumor markers may include alpha fetoprotein, apolipoprotein D, BAG-1 (RAP46 protein), CA19-9 (sialyl lewisa), CA50 (carcinoma associated mucin antigen), CA125 (ovarian cancer antigen), CA242 (tumour associated mucin antigen), chromogranin A, clusterin (apolipoprotein J), epithelial membrane antigen, epithelial-related antigen, epithelial specific antigen, gross cystic disease fluid protein-15, hepatocyte specific antigen, heregulin, human gastric mucin, human milk fat globule, MAGE-1, matrix metalloproteinases, melan A, melanoma target (HMB45), mesothelin, metallothionein, microphthalmia transcription factor (MITF), Muc-1 core glycoprotein. Muc-1 glycoprotein, Muc-2 glycoprotein, Muc-5AC glycoprotein, Muc-6 glycoprotein, myeloperoxidase, Myf-3 (Rhabdomyosarcoma target), Myf-4 (Rhabdomyosarcoma target), MyoD1 (Rhabdomyosarcoma target), myoglobin, nm23 protein, placental alkaline phosphatase, prealbumin, prostate specific antigen, prostatic acid phosphatase, prostatic inhibin peptide, PTEN, renal cell carcinoma target, small intestinal mucinous antigen, tetranectin, thyroid transcription factor-1, tissue inhibitor of matrix metalloproteinase 1, tissue inhibitor of matrix metalloproteinase 2, tyrosinase, tyrosinase-related protein-1, villin, or von Willebrand factor.

Suitable examples of cell cycle associated markers may include apoptosis protease activating factor-1, bcl-w, bcl-x, bromodeoxyuridine, CAK (cdk-activating kinase), cellular apoptosis susceptibility protein (CAS), caspase 2, caspase 8, CPP32 (caspase-3), CPP32 (caspase-3), cyclin dependent kinases, cyclin A, cyclin B1, cyclin D1, cyclin D2, cyclin D3, cyclin E, cyclin G, DNA fragmentation factor (N-terminus), Fas (CD95), Fas-associated death domain protein, Fas ligand, Fen-1, IPO-38, Mcl-1, minichromosome maintenance proteins, mismatch repair protein (MSH2), poly (ADP-Ribose) polymerase, proliferating cell nuclear antigen, p16 protein, p27 protein, p34cdc2, p57 protein (Kip2), p105 protein, Stat 1 alpha, topoisomerase I, topoisomerase II alpha, topoisomerase III alpha, or topoisomerase II beta.

Suitable examples of neural tissue and tumor markers may include alpha B crystallin, alpha-internexin, alpha synuclein, amyloid precursor protein, beta amyloid, calbindin, choline acetyltransferase, excitatory amino acid transporter 1, GAP43, glial fibrillary acidic protein, glutamate receptor 2, myelin basic protein, nerve growth factor receptor (gp75), neuroblastoma target, neurofilament 68 kD, neurofilament 160 kD, neurofilament 200 kD, neuron specific enolase, nicotinic acetylcholine receptor alpha4, nicotinic acetylcholine receptor beta2, peripherin, protein gene product 9, S-100 protein, serotonin, SNAP-25, synapsin I, synaptophysin, tau, tryptophan hydroxylase, tyrosine hydroxylase, or ubiquitin.

Suitable examples of cluster differentiation markers may include CD1a, CD1b, CD1c, CD1d, CD1e, CD2, CD3delta, CD3epsilon, CD3gamma, CD4, CD5, CD6, CD7, CD8alpha, CD8beta, CD9, CD10, CD11a, CD11b, CD11c, CDw12, CD13, CD14, CD15, CD15s, CD16a, CD16b, CDw17, CD18, CD19, CD20, CD21, CD22, CD23, CD24, CD25, CD26, CD27, CD28, CD29, CD30, CD31, CD32, CD33, CD34, CD35, CD36, CD37, CD38, CD39, CD40, CD41, CD42a, CD42b, CD42c, CD42d, CD43, CD44, CD44R, CD45, CD46, CD47, CD48, CD49a, CD49b, CD49c, CD49d, CD49e, CD49f, CD50, CD51, CD52, CD53, CD54, CD55, CD56, CD57, CD58, CD59, CDw60, CD61, CD62E, CD62L, CD62P, CD63, CD64, CD65, CD65s, CD66a, CD66b, CD66c, CD66d, CD66e, CD66f, CD68, CD69, CD70, CD71, CD72, CD73, CD74, CDw75, CDw76, CD77, CD79a, CD79b, CD80, CD81, CD82, CD83, CD84, CD85, CD86, CD87, CD88, CD89, CD90, CD91, CDw92, CDw93, CD94, CD95, CD96, CD97, CD98, CD99, CD100, CD101, CD102, CD103, CD104, CD105, CD106, CD107a, CD107b, CDw108, CD109, CD114, CD115, CD116, CD117, CDw119, CD120a, CD120b, CD121a, CDw121b, CD122, CD123, CD124, CDw125, CD126, CD127, CDw128a, CDw128b, CD130, CDw131, CD132, CD134, CD135, CDw136, CDw137, CD138, CD139, CD140a, CD140b, CD141, CD142, CD143, CD144, CDw145, CD146, CD147, CD148, CDw149, CDw150, CD151, CD152, CD153, CD154, CD155, CD156, CD157, CD158a, CD158b, CD161, CD162, CD163, CD164, CD165, CD166, and TCR-zeta.

Other suitable target proteins include centromere protein-F (CENP-F), giantin, involucrin, lamin A&C (XB 10), LAP-70, mucin, nuclear pore complex proteins, p180 lamellar body protein, ran, cathepsin D, Ps2 protein, Her2-neu, P53, S100, epithelial target antigen (EMA), TdT, MB2, MB3, PCNA, Ki67, cytokeratin, PI3K, cMyc or MAPK.

Still other suitable target proteins include Her2/neu (epidermal growth factor over expressed in breast and stomach cancer, therapy by a monoclonal antibody slows tumor growth); EGF-R/erbB (epidermal growth factor receptor); ER (estrogen receptor required for growth of some breast cancer tumors, located in the nucleus and detected with ISH for deciding on therapy limiting estrogen in positive patients); PR (progesterone receptor is a hormone that binds to DNA); AR (androgen receptor is involved in androgen dependent tumor growth); β-catenin (oncogene in cancer translocates from the cell membrane to the nucleus, which functions in both cell adhesion and as a latent gene regulatory protein); Phospho-β-Catenin: phosphorylated (form of β-catenin degrades in the cytosol and does not translocate to the nucleus); GSK3β (glycogen synthase kinase-3β protein in the Wnt pathway phosphorylates β-catenin marking the phospo-β-catenin for rapid degradation in the protostomes); PKCβ (mediator G-protein coupled receptor); NFKβ (nuclear factor kappa B marker for inflammation when translocated to the nucleus); VEGF (vascular endothelial growth factor related to angiogenesis); E-cadherin (cell to cell interaction molecule expressed on epithelial cells, the function is lost in epithelial cancers); c-met (tyrosine kinase receptor). In a preferred embodiment, the target protein is HER2.

Target Nucleic Acid Sequence

A target nucleic acid sequence according to an embodiment of the invention refers to a sequence of interest which is contained in a nucleic acid molecule in the biological sample. The nucleic acid molecule may be present in the nuclei of the cells of the biological sample (for example, chromosomal DNA) or present in the cytoplasm (for example, mRNA). In some embodiments, a nucleic acid molecule may not be inherently present on the surface of a biological sample and the biological sample may have to be processed to make the nucleic acid molecule accessible by a probe. For example, protease treatment of the sample could readily bring the target nucleic acid sequences.

Suitability of a nucleic acid molecule to be analyzed may be determined by the type and nature of analysis required for the biological sample. In some embodiments, the analysis may provide information about the gene expression level of the target nucleic acid sequence in the biological sample. In other embodiments, the analysis may provide information on the presence or absence or amplification level of a chromosomal DNA. For example, if the biological sample includes a tissue sample, the methods disclosed herein may be used to detect a target nucleic acid sequence that may identify cells which has an increased copy number of a particular chromosomal segment harboring the target nucleic acid sequence.

In some embodiments, the target nucleic acid sequence in a tissue sample that may be detected and analyzed using the methods disclosed herein may include, but are not limited to, nucleic acid sequences for prognostic markers, hormone or hormone receptors, lymphoids, tumor markers, cell cycle associated markers, neural tissue and tumor markers, or cluster differentiation markers. Examples of these markers are described in the section entitled "Target proteins". For example, in one embodiment, the target nucleic acid sequence target is a sequence for the EGFR, TOP2A, cMyc, ALK, FGFR1 or HER2 gene.

In certain embodiments, the target nucleic acid sequence includes a sequence that is part of the gene sequence which encodes the target protein. In other embodiments, the target nucleic acid sequence does not include a sequence that is part of the gene sequence which encodes the target protein. Thus, the target nucleic acid sequence may include a sequence that is part of the gene sequence which encodes a different protein than the target protein.

Probes for the Target Nucleic Acid Sequences

In some embodiments, a probe is used to detect the target nucleic acid sequences. It is desirable that the probe binds specifically to the region of nucleic acid molecule that contains the sequence of interest. Thus, in some embodiments, the probe is sequence-specific. A sequence-specific probe may include a nucleic acid and the probe may be capable of recognizing a particular linear arrangement of nucleotides or derivatives thereof. In some embodiments, the linear arrangement may include contiguous nucleotides or derivatives thereof that may each bind to a corresponding complementary nucleotide in the probe. In an alternate embodiment, the sequence may not be contiguous as there may be one, two, or more nucleotides that may not have corresponding complementary residues on the probe. Suitable examples of probes may include, but are not limited to DNA or RNA oligonucleotides or polynucleotides, peptide nucleic acid sequences, locked nucleic acid (LNA) sequences, or aptamers. In some embodiments, suitable probes may include nucleic acid analogs, such as dioxygenin dCTP, biotin dcTP 7-azaguanosine, azidothymidine, inosine, or uridine.

In some embodiments, a probe may form a Watson-Crick bond with the target nucleic acid sequence. In another embodiment, the probe may form a Hoogsteen bond with the target nucleic acid sequence, thereby forming a triplex. A probe that binds by Hoogsteen binding may enter the major groove of a nucleic acid sequence and hybridizes with the bases located there. In certain embodiments, the probes may form both Watson-Crick and Hoogsteen bonds with the target nucleic acid sequence (for example, bis PNA probes are capable of both Watson-Crick and Hoogsteen binding to a nucleic acid molecule).

In some embodiments, the probe may comprise a nucleic acid probe, a peptide nucleic acid probe, a locked nucleic acid (LNA) probe, mRNA probe, miRNA probe or siRNA probe.

The length of the probe may also determine the specificity of binding. The energetic cost of a single mismatch between the probe and the target nucleic acid sequence may be relatively high for shorter sequences than for longer ones. In some embodiments, hybridization of smaller probes may be more specific than the hybridization of longer probes, as the longer probes may be more amenable to mismatches and may continue to bind to the nucleic acid depending on the conditions. In certain embodiments, shorter probes may exhibit lower binding stability at a given temperature and salt concentration. Probes that may exhibit greater stability to bind short sequences may be employed in this case (for examples, bis PNA). In some embodiments, the probe may have a length in range of from about 4 nucleotides to about 12 nucleotides, from about 12 nucleotides to about 25 nucleotides, from about 25 nucleotides to about 50 nucleotides, from about 50 nucleotides to about 100 nucleotides, from about 100 nucleotides to about 250 nucleotides, from about 250 nucleotides to about 500 nucleotides, or from about 500 nucleotides to about 1000 nucleotides. In some embodiments, the probe may have a length in a range that is greater than about 1000 nucleotides. Notwithstanding the length of the probe, all the nucleotide residues of the probe may not hybridize to complementary nucleotides in the target nucleic acid sequence. For example, the probe may include 50 nucleotide residues in length, and only 25 of those residues may hybridize to the target nucleic acid sequence. In some embodiments, the nucleotide residues that may hybridize may be contiguous with each other. The probe may be single stranded or may include a secondary structure.

In some embodiments, a biological sample may include a cell or a tissue sample and the biological sample may be subjected to in situ hybridization (ISH) using a probe. In some embodiments, a tissue sample may be subjected to in situ hybridization in addition to immunofluorescence (IF) to obtain desired information regarding the tissue sample.

Regardless of the type of probe and the target nucleic acid sequence, the specificity of binding between the probe and the nucleic acid sequence may also be affected depending on the binding conditions (for example, hybridization conditions in case of complementary nucleic acids. Suitable binding conditions may be realized by modulating one or more of pH, temperature, or salt concentration.

A probe may be intrinsically labeled (fluorophore attached during synthesis of probe) with a fluorophore or extrinsically labeled (fluorophore attached during a later step). For example, an intrinsically labeled nucleic acid may be synthesized using methods that incorporate fluorophore-labeled nucleotides directly into the growing nucleic acid chain. In some embodiments, a probe may be synthesized in a manner such that fluorophores may be incorporated at a later stage. For example, this latter labeling may be accomplished by chemical means by the introduction of active amino or thiol groups into nucleic acids chains. In some embodiments, a probe such a nucleic acid (for example, a DNA) may be directly chemically labeled using appropriate chemistries for the same.

Binders

The methods disclosed herein involve the use of binders that physically bind to the target in a specific manner. In some embodiments, a binder may bind to a target with sufficient specificity, that is, a binder may bind to a target with greater affinity than it does to any other molecule. In some embodiments, the binder may bind to other molecules, but the binding may be such that the non-specific binding may be at or near background levels. In some embodiments, the affinity of the binder for the target of interest may be in a range that is at least 2-fold, at least 5-fold, at least 10-fold, or more than its affinity for other molecules. In some embodiments, binders with the greatest differential affinity may be employed, although they may not be those with the greatest affinity for the target.

Binding between the target and the binder may be affected by physical binding. Physical binding may include binding effected using non-covalent interactions. Non-covalent interactions may include, but are not limited to, hydrophobic interactions, ionic interactions, hydrogen-bond interactions, or affinity interactions (such as, biotin-avidin or biotin-streptavidin complexation). In some embodiments, the target and the binder may have areas on their surfaces or in cavities giving rise to specific recognition between the two resulting in physical binding. In some embodiments, a binder may bind to a biological target based on the reciprocal fit of a portion of their molecular shapes.

Binders and their corresponding targets may be considered as binding pairs, of which non-limiting examples include immune-type binding-pairs, such as, antigen/antibody, antigen/antibody fragment, or hapten/anti-hapten; nonimmune-type binding-pairs, such as biotin/avidin, biotin/streptavidin, folic acid/folate binding protein, hormone/hormone receptor, lectin/specific carbohydrate, enzyme/enzyme, enzyme/substrate, enzyme/substrate analog, enzyme/pseudo-substrate (substrate analogs that cannot be catalyzed by the enzymatic activity), enzyme/co-factor, enzyme/modulator, enzyme/inhibitor, or vitamin B12/intrinsic factor. Other suitable examples of binding pairs may include complementary nucleic acid fragments (including DNA sequences, RNA sequences, PNA sequences, and peptide nucleic acid sequences, locked nucleic acid (LNA) sequences); Protein A/antibody; Protein G/antibody; nucleic acid/nucleic acid binding protein; or polynucleotide/polynucleotide binding protein.

In some embodiments, the binder may be a sequence- or structure-specific binder, wherein the sequence or structure of a target recognized and bound by the binder may be sufficiently unique to that target.

In some embodiments, the binder may be structure-specific and may recognize a primary, secondary, or tertiary structure of a target. A primary structure of a target may include specification of its atomic composition and the chemical bonds connecting those atoms (including stereochemistry), for example, the type and nature of linear arrangement of amino acids in a protein. A secondary structure of a target may refer to the general three-dimensional form of segments of biomolecules, for example, for a protein a secondary structure may refer to the folding of the peptide "backbone" chain into various conformations that may result in distant amino acids being brought into proximity with each other. Suitable examples of secondary structures may include, but are not limited to, alpha helices, beta pleated sheets, or random coils. A tertiary structure of a target may be is its overall three dimensional structure. A quaternary structure of a target may be the structure formed by its noncovalent interaction with one or more other targets or macromolecules (such as protein interactions). An example of a quaternary structure may be the structure formed by the four-globin protein subunits to make hemoglobin. A binder in accordance with the embodiments of the invention may be specific for any of the afore-mentioned structures.

An example of a structure-specific binder may include a protein-specific molecule that may bind to a protein target. Examples of suitable protein-specific molecules may include antibodies and antibody fragments, nucleic acids (for example, aptamers that recognize protein targets), or protein substrates (non-catalyzable).

In some embodiments, a target may include an antigen and a binder may include an antibody. A suitable antibody may include monoclonal antibodies, polyclonal antibodies, multispecific antibodies (for example, bispecific antibodies), or antibody fragments so long as they bind specifically to a target antigen.

In some embodiments, a target may include a monoclonal antibody. A "monoclonal antibody" may refer to an antibody obtained from a population of substantially homogeneous antibodies, that is, the individual antibodies comprising the population are identical except for possible naturally occurring mutations that may be present in minor amounts. Monoclonal antibodies may be highly specific, being directed against a single antigenic site. Furthermore, in contrast to (polyclonal) antibody preparations that typically include different antibodies directed against different determinants (epitopes), each monoclonal antibody may be directed against a single determinant on the antigen. A monoclonal antibody may be prepared by any known method such as the hybridoma method, by recombinant DNA methods, or may be isolated from phage antibody libraries.

In some embodiments, a biological sample may include a cell or a tissue sample and the methods disclosed herein may be employed in immunofluorescence (IF). Immunochemistry may involve binding of a target antigen to an antibody-based binder to provide information about the tissues or cells (for example, diseased versus normal cells). Examples of antibodies (and the corresponding diseases/disease cells) suitable as binders for methods disclosed herein include, but are not limited to, anti-estrogen receptor antibody (breast cancer), anti-progesterone receptor antibody (breast cancer), anti-p53 antibody (multiple cancers), anti-Her-2/neu antibody (multiple cancers), anti-EGFR antibody (epidermal growth factor, multiple cancers), anti-cathepsin D antibody (breast and other cancers), anti-Bcl-2 antibody (apoptotic cells), anti-E-cadherin antibody, anti-CA125 antibody (ovarian and other cancers), anti-CA15-3 antibody (breast cancer), anti-CA19-9 antibody (colon cancer), anti-c-erbB-2 antibody, anti-P-glycoprotein antibody (MDR, multi-drug resistance), anti-CEA antibody (carcinoembryonic antigen), anti-retinoblastoma protein (Rb) antibody, anti-ras oneoprotein (p21) antibody, anti-Lewis X (also called CD15) antibody, anti-Ki-67 antibody (cellular proliferation), anti-PCNA (multiple cancers) antibody, anti-CD3 antibody (T-cells), anti-CD4 antibody (helper T cells), anti-CD5 antibody (T cells), anti-CD7 antibody (thymocytes, immature T cells, NK killer cells), anti-CD8 antibody (suppressor T cells), anti-CD9/p24 antibody (ALL), anti-CD10 (also called CALLA) antibody (common acute lymphoblasic leukemia), anti-CD11c antibody (Monocytes, granulocytes, AML), anti-CD13 antibody (myelomonocytic cells, AML), anti-CD14 antibody (mature monocytes, granulocytes), anti-CD15 antibody (Hodgkin's disease), anti-CD19 antibody (B cells), anti-CD20 antibody (B cells), anti-CD22 antibody (B cells), anti-CD23 antibody (activated B cells, CLL), anti-CD30 antibody (activated T and B cells, Hodgkin's disease), anti-CD31 antibody (angiogenesis marker), anti-CD33 antibody (myeloid cells, AML), anti-CD34 antibody (endothelial stem cells, stromal tumors), anti-CD35 antibody (dendritic cells), anti-CD38 antibody (plasma cells, activated T, B, and myeloid cells), anti-CD41 antibody (platelets, megakaryocytes), anti-LCA/CD45 antibody (leukocyte common antigen), anti-CD45RO antibody (helper, inducer T cells), anti-CD45RA antibody (B cells), anti-CD39, CD100 antibody, anti-CD95/Fas antibody (apoptosis), anti-CD99 antibody (Ewings Sarcoma marker, MIC2 gene product), anti-CD106 antibody (VCAM-1; activated endothelial cells), anti-ubiquitin antibody (Alzheimer's disease), anti-CD71 (transferrin receptor) antibody, anti-c-myc (oncoprotein and a hapten) antibody, anti-cytokeratins (transferrin receptor) antibody, anti-vimentins (endothelial cells) antibody (B and T cells), anti-HPV proteins (human papillomavirus) antibody, anti-kappa light chains antibody (B cell), anti-lambda light chains antibody (B cell), anti-melanosomes (HMB45) antibody (melanoma), anti-prostate specific antigen (PSA) antibody (prostate cancer), anti-S-100 antibody (melanoma, salvary, glial cells), anti-tau antigen antibody (amyloid associated disease), anti-fibrin antibody (epithelial cells), anti-keratins antibody, anti-cytokeratin antibody (tumor), anti-alpha-catenin (cell membrane), or anti-Tn-antigen antibody (colon carcinoma, adenocarcinomas, and pancreatic cancer).

Other specific examples of suitable antibodies may include, but are not limited to, anti proliferating cell nuclear antigen, clone pc10 (Sigma Aldrich, P8825); anti smooth muscle alpha actin (SmA), clone 1A4 (Sigma, A2547); rabbit anti beta catenin (Sigma, C 2206); mouse anti pan cytokeratin, clone PCK-26 (Sigma, C1801); mouse anti estrogen receptor alpha, clone 1D5 (DAKO, M 7047); beta catenin antibody, clone 15B8 (Sigma, C 7738); goat anti vimentin (Sigma, V4630); cycle androgen receptor clone AR441 (DAKO, M3562); Von Willebrand Factor 7, keratin 5, keratin 8/18, e-cadherin, Her2/neu, Estrogen receptor, p53, progesterone receptor, beta catenin; donkey anti-mouse (Jackson Immunoresearch, 715-166-150); or donkey anti rabbit (Jackson Immunoresearch, 711-166-152).

Regardless of the type of binder and the target, the specificity of binding between the binder and the target may also be affected depending on the binding conditions (for example, hybridization conditions in case of complementary nucleic acids). Suitable binding conditions may be realized by modulating one or more of pH, temperature, or salt concentration.

As noted hereinabove, a binder may be intrinsically labeled (fluorophore attached during synthesis of binder) with a fluorophore or extrinsically labeled (fluorophore attached during a later step). For example for a protein-based binder, an intrinsically labeled binder may be prepared by employing fluorophore labeled amino acids. In some embodiments, a binder may be synthesized in a manner such that fluorophore may be incorporated at a later stage. In some embodiments, a binder such a protein (for example, an antibody) or a nucleic acid (for example, a DNA) may be directly chemically labeled using appropriate chemistries for the same.

In some embodiments, combinations of binders may be used that may provide greater specificity or in certain embodiments amplification of the signal. Thus, in some embodiments, a sandwich of binders may be used, where the first binder may bind to the target and serve to provide for secondary binding, where the secondary binder may or may not include a fluorophore, which may further provide for tertiary binding (if required) where the tertiary binding member may include a fluorophore.

Suitable examples of binder combinations may include primary antibody-secondary antibody, complementary nucleic acids, or other ligand-receptor pairs (such as biotin-streptavidin). Some specific examples of suitable binder pairs may include mouse anti-myc for recombinant expressed proteins with c-myc epitope; mouse anti-HisG for recombinant protein with His-Tag epitope, mouse anti-xpress for recombinant protein with epitope-tag, rabbit anti-goat for goat IgG primary molecules, complementary nucleic acid sequence for a nucleic acid; mouse anti-thio for thioredoxin fusion proteins, rabbit anti-GFP for fusion protein, jacalin for α-D-galactose; and melibiose for carbohydrate-binding proteins, sugars, nickel couple matrix or heparin.

In some embodiments, a combination of a primary antibody and a secondary antibody may be used as a binder. A primary antibody may be capable of binding to a specific region of the target and the secondary antibody may be capable of binding to the primary antibody. A secondary antibody may be attached to a fluorophore before binding to the primary antibody or may be capable of binding to a fluorophore at a later step. In an alternate embodiment, a primary antibody and specific binding ligand-receptor pairs (such as biotin-streptavidin) may be used. The primary antibody may be attached to one member of the pair (for example biotin) and the other member (for example streptavidin) may be labeled with a fluorophore. The secondary antibody, avidin, streptavidin, or biotin may be each independently labeled with a fluorophore.

In some embodiments, the methods disclosed herein may be employed in an immunofluorescence procedure, and a primary antibody may be used to specifically bind the target antigen in the tissue sample. A secondary antibody may be used to specifically bind to the primary antibody, thereby forming a bridge between the primary antibody and a subsequent reagent (for example a fluorophore), if any. For example, a primary antibody may be mouse IgG (an antibody created in mouse) and the corresponding secondary antibody may be goat anti-mouse (antibody created in goat) having regions capable of binding to a region in mouse IgG.

In some embodiments, signal amplification may be obtained when several secondary antibodies may bind to epitopes on the primary antibody. In an immunofluorescence procedure a primary antibody may be the first antibody used in the procedure and the secondary antibody may be the second antibody used in the procedure. In some embodiments, a primary antibody may be the only antibody used in an IF procedure.

Generating a First Image of the Biological Sample

In certain embodiments of the invention, the method comprises a step of generating a first image of the biological sample. The first image is generated by (a) contacting the sample, on a solid support, with a first binder for a target protein; (b) staining the sample with a fluorescent marker that provides morphological information; (c) detecting, by fluorescence, signals from the first binder and the fluorescent marker; and (d) generating the first image of at least part of the sample from the detected fluorescent signals. In certain embodiments, steps (a) and (b) constitutes the first protocol. In certain embodiments, the method also comprises, in the first step, contacting the sample with at least one additional binder that provides additional morphological information; and detecting signals from the at least one additional binder by fluorescence. In certain embodiments, step (c) also comprises detecting, by fluorescence, an endogenous fluorescence signal (also known as autofluorescence) originating from such structures as red blood cells, fibroses, and lipofuscin granules. In certain embodiments, generating the first image (step (d)) comprises, generating an initial image at lower magnification of at least part of the sample from the detected fluorescent signals; selecting a region of interest from the initial image, and detecting by fluorescence, signals from at least the first binder and the fluorescent marker to generate the first image at a higher resolution than the initial image. By "selecting a region of interest", it is understood to mean (1) a user selects a region of interest based on the initial image; (2) the computer (i.e., imaging system implementing the method) selects a region of interest based on the initial image, an algorithm, and an instruction it received; or (3) the computer selects a region of interest based on the initial image and an algorithm. It is to be understood that the first image does not necessarily refer to the initial image generated. Similarly, the second image does not literally refer to the very second image generated by the embodiments of the method.

In certain embodiments, the method of generating a first image of the biological sample comprises the steps of: (a) contacting the sample on a solid support with a first binder for a target protein; (b) staining the sample with a fluorescent marker that provides morphological information; (c) detecting, by fluorescence, signals from the first binder and the fluorescent marker; and (d) generating the first image of at least part of the sample from the detected fluorescent signals of the first binder and optionally the fluorescent marker. Accordingly, in such an embodiment, the first image may be used to identify the target protein in the sample whilst signals acquired from the fluorescent marker are acquired in order to allow images to be registered as defined herein.

In certain embodiments, the initial image may be one or more brightfield type images that resemble a brightfield staining protocol. Thus, the initial fluorescence image data may be used to generate a simulated (virtual/molecular) hematoxylin and eosin (H&E) image via an algorithm. Alternatively, a simulated (virtual/molecular) 3,3'-Diaminobenzidine (DAB) image may be generated via a similar algorithm. Detailed methods for converting fluorescence image data into a brightfield type image is described hereinbelow under the heading "*Image Acquisition and Analysis*". The brightfield type image is then used for the selection of the region of interest.

In some embodiments, a biological sample may include a whole cell, a tissue sample or a microarray. In some embodiments, a biological sample may include a tissue sample. The tissue sample may be obtained by a variety of procedures including, but not limited to surgical excision, aspiration or biopsy. The tissue may be fresh or frozen. In some embodiments, the tissue sample may be fixed and embedded in paraffin. The tissue sample may be fixed or otherwise preserved by conventional methodology; the choice of a fixative may be determined by the purpose for which the tissue is to be histologically stained or otherwise analyzed. The length of fixation may depend upon the size of the tissue sample and the fixative used. For example, neutral buffered formalin, Bouin's or paraformaldehyde, may be used to fix or preserve a tissue sample.

In some embodiments, the tissue sample may be first fixed and then dehydrated through an ascending series of alcohols, infiltrated and embedded with paraffin or other sectioning media so that the tissue sample may be sectioned. In an alternative embodiment, a tissue sample may be sectioned and subsequently fixed. In some embodiments, the tissue sample may be embedded and processed in paraffin. Examples of paraffin that may be used include, but are not limited to, Paraplast, Broloid, and Tissuecan. Once the tissue sample is embedded, the sample may be sectioned by a microtome into sections that may have a thickness in a range of from about three microns to about five microns. Once sectioned, the sections may be attached to slides using adhesives. Examples of slide adhesives may include, but are not limited to, silane, gelatin, poly-L-lysine. In certain embodiments, if paraffin is used as the embedding material, the tissue sections may be deparaffinized and rehydrated in water. The tissue sections may be deparaffinized, for example, by using organic agents (such as, xylenes or gradually descending series of alcohols).

In some embodiments, aside from the sample preparation procedures discussed above, the tissue section may be subjected to further treatment prior to, during, or following immunofluorescence assay. For example, in some embodiments, the tissue section may be subjected to epitope (i.e., antigen) retrieval methods, such as, heating of the tissue sample in citrate buffer. In some embodiments, a tissue section may be optionally subjected to a blocking step to minimize any non-spec ific binding.

Following the preparation of the sample, the sample may be contacted with a binder solution (e.g., labeled-antibody solution in an immunofluorescence procedure) for a sufficient period of time and under conditions suitable for binding of binder to the target protein (e.g., antigen in an immunofluorescence procedure). In some embodiments, the biological sample may be contacted with more than one binder in the contacting step. The plurality of binders may be capable of binding different target proteins in the biological sample. For example, a biological sample may include two target proteins: target1 and target2 and two sets of binders may be used in this instance: binders1 (capable of binding to target1) and binders2 (capable of binding to target2). A plurality of binders may be contacted with the biological sample simultaneously (for example, as a single mixture).

In addition to contacting the sample with one or more binders for one or more targets, the sample may also be stained with at least one additional binder that provides morphological information. In one embodiment, the binders that provide morphological information may be included simultaneously with the binders for the targets. In other embodiments, they may be used to stain the sample after the binder-target reaction.

The morphological information includes, but is not limited to, tissue morphology information such as tissue type and origin, information about the origin of certain cells, information about subcellular structure of cells such an membrane, cytoplasm or nucleus, information about cell differentiation state, cell cycle stage, cell metabolic status, cell necrosis or apoptosis, cell types, and tumor, normal, and stromal regions. For example, the morphological information may comprise information about cytoplasm location of cells of epithelial origin or it may indicate location of poorly differentiated or necrotic region of a tumor.

The morphological information may be provided by the at least one additional binder which bind to specific targets in the biological sample. In some embodiments the at least one additional binder is an antibody that binds to, but is not limited to, the following target protein:

Cytokeratin: marker for epithelial cells
Pan-cadherin: marker for the cell membrane
Na+K+ATPase marker for cell membrane
Smooth muscle actin: smooth muscle cells, myofibroblasts and myoepithelial cells
CD31 marker for blood vessels
Ribosomal protein S6: marker for cytoplasm
Glut 1 marker for hypoxia
Ki67 marker for proliferating cells
Collagen IV stroma Other targets that provides morphological information may also include keratin 15, 19, E-cadherin, Claudin 1, EPCAM, fibronectin and vimentin.

The endogenous fluorescence (autofluorescence) of tissue may be used to provide additional morphological information including, but not limited to, red blood cells, lipofuscin granules, and fibroses in the sample under study.

As an example, the at least one additional binder may comprise pan-cytokeratin antibodies (e.g., a cocktail of cytokeratin antibodies that allow greater coverage of cytokeratin isoforms in one reaction). The cytokeratin is a part of the cytoskeleton and is located in the cytoplasm of cells in the epithelium. Thus, these antibodies stain the cytoplasm of epithelium cells. In a tumor sample, these antibodies stain epithelial cells of the tumor, as opposed to stroma or other support tissue/region. Thus, the use of the at least one additional binder such as pan-cytokeratin markers allows the selection of epithelial cell regions of the tumor for further analysis.

Preferably, the binders are labeled with fluorophores. When more than one target are detected, the binders for each target are preferably labeled with different fluorophores which have different emission wavelengths such that the signals can be independently detected and do not overlap substantially. Also preferably, the binders that provide morphological information are also labeled with different fluorophores from the other binders such that they have different emission wavelengths as well.

After a sufficient time has been provided for the binding action, the sample may be contacted with a wash solution (for example an appropriate buffer solution) to wash away any unbound probes. Depending on the concentration and type of probes used, a biological sample may be subjected to a number of washing steps with the same or different washing solutions being employed in each step.

Following the reaction between the binders and the target proteins and the optional morphological markers, the sample is further stained with a fluorescent marker that provides additional morphological information. The term "fluorescent marker" refers to a fluorophore which selectively stains particular parts of a tissue or other biological sample, such as certain subcellular morphology. Examples of suitable fluorescent marker (and their target cells, subcellular compartments, or cellular components if applicable) may include, but are not limited to: 4',6-diamidino-2-phenylindole (DAPI) (nucleic acids), Eosin (alkaline cellular components, cytoplasm), Hoechst 33258 and Hoechst 33342 (two bisbenzimides) (nucleic acids), Propidium Iodide (nucleic acids), Quinacrine (nucleic acids), Fluorescein-phalloidin (actin fibers), Chromomycin A 3 (nucleic acids), Acriflavine-Feulgen reaction (nucleic acid), Auramine O-Feulgen reaction (nucleic acids), Ethidium Bromide (nucleic acids). Nissl stains (neurons), high affinity DNA fluorophores such as POPO, BOBO, YOYO and TOTO and others, and Green Fluorescent Protein fused to DNA binding protein (e.g., histones), ACMA, and Acridine Orange. Preferably, the fluorescent marker stains the nucleus. More preferably, the fluorescent marker comprises 4',6-diamidino-2-phenylindole (DAPI).

The total number of binders and fluorescent marker that may be applied to a biological sample may depend on the spectral resolution achievable by the spectrally resolvable fluorescent signals from the fluorophores used. Spectrally resolvable, in reference to a plurality of fluorophores, implies that the fluorescent emission bands of the fluorophores are sufficiently distinct, that is, sufficiently non-overlapping, such that, the respective fluorophores may be distinguished on the basis of the fluorescent signal generated by each fluorophore using standard photodetection systems. In some embodiments, a biological sample may be reacted with ten or less than ten fluorophores in each round of detection by a detection system. In other embodiments, a biological sample may be reacted with six or less than six fluorophores in each round of detection by a detection system.

Signals from the binder-labeled fluorophores, the fluorescent marker, and the autofluorescence of the sample may be detected using a detection system. The detection system may include a fluorescent detection system. In some embodiments, signal intensity, signal wavelength, signal location, signal frequency, or signal shift may be determined. In some embodiments, one or more aforementioned characteristics of the signal may be observed, measured, and recorded. In some embodiments, fluorescence wavelength or fluorescent intensity may be determined using a fluorescent detection system. In some embodiments, a signal may be observed in situ, that is, a signal may be observed directly from the fluorophore associated through the binder to the target in the biological sample.

In some embodiments, observing a signal may include capturing an image of the biological sample. In some embodiments, a microscope connected to an imaging device may be used as a detection system, in accordance with the methods disclosed herein. In some embodiments, a fluorophore may be excited and the fluorescent signal obtained may be observed and recorded in the form of a digital signal (for example, a digitalized image). The same procedure may be repeated for different fluorophores that are bound in the sample, and for the autofluorescence of the sample, using the appropriate fluorescence filters.

Additional details about the method and system for fluorescence detection, as well as the method and system for generating a first image of the sample are provided hereinbelow under the heading "Image Acquisition and Analysis".

In some embodiments, after the first image of the biological sample is generated from the detected fluorescent signals, the fluorescent signals from the binders are modified. Thereafter, one or more additional images are obtained according to the method described above. Namely, each additional image is generated by (a) contacting the sample on a solid support with a binder for a different target protein; (b) staining the sample with the fluorescent marker that provides additional morphological information; (c) detecting, by fluorescence, signals from the binder and the fluorescent marker; and (d) generating an image of the sample from the detected fluorescent signals.

A chemical agent may be applied to the biological sample to modify the fluorescent signal. In some embodiments, signal modification may include one or more of a change in signal characteristic, for example, a decrease in intensity of signal, a shift in the signal peak, a change in the resonant frequency, or cleavage (removal) of the signal generator resulting in signal removal. Such chemical agents are known to person skilled in the art, for example, see U.S. Pat. No. 7,629,125.

In some embodiments, a chemical agent may be in the form of a solution and the biological sample may be contacted with the chemical agent solution for a predetermined amount of time. The concentration of the chemical agent solution and the contact time may be dependent on the type of signal modification desired. In some embodiments, the contacting conditions for the chemical agent may be selected such that the binder, the target, the biological sample, and binding between the binder and the target may not be affected. In some embodiments, a chemical agent may only affect the fluorophore and the chemical agent may not affect the target/binder binding or the binder integrity. Thus by way of example, a binder may include a primary antibody or a primary antibody/secondary combination. A chemical agent may only affect the fluorophore, and the primary antibody or primary antibody/secondary antibody combination may essentially remain unaffected. In some embodiments, a binder (such as, a primary antibody or primary antibody/ secondary antibody combination) may remain bound to the target in the biological sample after contacting the sample with the chemical agent. In some embodiments, a binder may remain bound to the target in the biological sample after contacting the sample with the chemical agent and the binder integrity may remain essentially unaffected (for example, an antibody may not substantially denature or elute in the presence of a chemical agent).

In some embodiments, a characteristic of the signal may be observed after contacting the sample with a chemical agent to determine the effectiveness of the signal modification. For example, fluorescence intensity from a fluorescent signal generator may be observed before contacting with the chemical agent and after contacting with the chemical agent. In some embodiments, a decrease in signal intensity by a predetermined amount may be referred to as signal modification. In some embodiments, modification of the signal may refer to a decrease in the signal intensity by an amount in a range of greater than about 50 percent. In some embodiments, modification of the signal may refer to a decrease in the signal intensity by an amount in a range of greater than about 60 percent. In some embodiments, modification of the signal may refer to a decrease in signal intensity by an amount in a range of greater than about 80 percent. In certain embodiments, the signal modification may be accomplished through oxidation, stripping, photobleaching, or a mixture thereof. In a preferred embodiment, the chemical agent is selected from the group consisting of sodium hydroxide, hydrogen peroxide, or sodium periodate. In another embodiment signal modification may be accomplished by contacting the sample with light and/or chemical agent, as described more fully in U.S. patent application Ser. No. 13/336,409 entitled "PHOTOACTIVATED CHEMICAL BLEACHING OF DYES FOR USE IN SEQUENTIAL ANALYSIS OF BIOLOGICAL SAMPLES" and filed on Dec. 23, 2011, herein incorporated by reference in its entirety.

Generating a Second Image of the Biological Sample

In certain embodiments of the invention, the method comprises a step of generating a second image of the biological sample. The second image is generated after the first image is obtained. The second image may be generated by (a) contacting the sample with a probe for each of at least one target nucleic acid sequences thus hybridizing the probes with the nucleic acid sequences; (b) optionally, staining the sample with the fluorescent marker used in generating the first image; (c) detecting, by fluorescence, signals from the probes for each of the target nucleic acid sequences and the fluorescent marker; and (d) generating a second image of the sample from the detected fluorescent signal or signals. In certain embodiments, steps (a) and (b) constitutes the second protocol.

The second image may also be generated by (a) contacting the sample with a binder for a different target protein; (b) optionally, staining the sample with the fluorescent marker used in generating the first image; (c) detecting, by fluorescence, signals from the probes for each of the target protein and the fluorescent marker; and (d) generating a second image of the sample from the detected fluorescent signal or signals. In the case where the second protocol is an immunofluorescence protocol, essentially the same steps are performed as described above for generating the first image. In certain embodiments, steps (a) and (b) constitutes the second protocol.

In certain embodiments, after the first image is obtained and prior to the step of generating the second image, the method comprises modifying the fluorescent signal from the first binder. In certain embodiments, the signal modification may be accomplished through oxidation, stripping, photobleaching, or a mixture thereof. In a preferred embodiment, the chemical agent is selected from the group consisting of sodium hydroxide, hydrogen peroxide, or sodium periodate.

In certain embodiments, after the first image is obtained and prior to the step of generating the second image, the method further comprises digesting the sample by a protease. The breaking of peptide bindings by protease digestion directly affects signal quality as it eases access of the probes to the target nucleic acid and reduces autofluorescence generated by intact proteins. Protease digestion also serves to remove the binder from the target protein(s) and therefore removes the immunofluorescence signal associated with the first image. An exemplary protease for a protease digest is a serine protease such as proteinase K. Another exemplary protease is a carboxyl protease, such as pepsin.

The target nucleic acid sequences and the probes are described in detail above. Preferably, the probes are fluorescently labeled.

In certain embodiments, the target nucleic acid sequence comprises genomic variations at the chromosomal level. In certain embodiments, the genomic variations are chromosomal abnormalities. Exemplary chromosomal abnormalities include chromosomal translocation, chromosomal deletions, chromosomal insertions and chromosomal inversions, as well as gene amplification events. In other embodiments, the target nucleic acid sequence comprises genomic variations at the individual gene level, such as single nucleotide polymorphisms, small deletions, insertions, as well as point mutations.

In certain embodiments, the probes are hybridized to the complementary strand of the target nucleic acid sequence within the biological sample. The probes and the target nucleic acid sequences may form hybrids under suitable hybridization conditions. Those of ordinary skill in the art of hybridization will recognize that factors commonly used to impose or control stringency of hybridization include formamide concentration (or other chemical denaturant reagent), salt concentration (i.e., ionic strength), hybridization temperature, detergent concentration, pH and the presence or absence of chaotropes. Blocking probes can also be used as a means to improve discrimination beyond the limits possible by mere optimization of stringency factors. Optimal stringency for forming a hybrid combination can be found by the well-known technique of fixing several of the aforementioned stringency factors and then determining the effect of varying a single stringency factor. The same stringency factors can be modulated to thereby control the stringency of hybridization of a PNA or LNA to a nucleic acid, except that the hybridization of a PNA is fairly independent of ionic strength. Optimal or suitable stringency for an assay can be experimentally determined by examination of each stringency factor until the desired degree of discrimination is achieved.

Methods for the detection of nucleic acid sequence such as hybridization are well known. In certain embodiments, a specific nucleic acid sequence is detected by FISH (or a variation of FISH such as IQ-FISH) or polymerase chain reaction (PCR) (or a variation of PCR such as in-situ PCR), RCA (rolling circle amplification) or PRINS (primed in situ labeling). In an exemplary embodiment, the specific nucleic acid sequence is detected by FISH. Thus, the target nucleic acid sequence in the biological sample is denatured and hybridizes, in situ, with a denatured fluorescently labeled probe. In certain preferred embodiments, when the target nucleic acid sequence is analyzed by FISH, a chromosome specific probe, such as a centromere probe for the same chromosome, is used, together with the probe for the target nucleic acid sequence. The signal from a chromosome specific probe shows whether the target nucleic acid sequence is on the same chromosome. Preferably, the chromosome specific probes are labeled with a fluorophore which generate a signal distinct from that of the probe for the target nucleic acid sequence.

Following the hybridization reaction, the sample is optionally stained with the fluorescent marker which provides additional morphological information. The fluorescent marker preferably is the same as used for obtaining the first image. Alternatively, the fluorescent marker is different but stains the same subcellular compartment as that used for obtaining the first image. In certain embodiments, fluorescent signal from the staining for the first image is sufficiently retained so this step is optional. In other embodiments, the fluorescent signal from the staining for the first image has faded and the sample is stained as provided here.

In certain embodiments, it is preferred that the fluorescent marker stains the nucleus of the cell. Thus the staining assists the focusing of the FISH signal. By obtaining the focused nucleus, the FISH signals can be captured by imaging several focal planes above and below the focused nucleus. The staining also assists the counting of the FISH signals. Since FISH signals may be scattered throughout the nucleus, dot counting performed using a single focal plane may lead to missed counts. However, by capturing several z-stacks within each field of view, it provides more data to generate, as close as possible, a three dimensional view of the nucleus. Therefore it is provided a more accurate method of counting FISH signals.

Staining the biological sample with the same fluorescent marker or fluorescent markers that stain the same subcellular compartment also serves to provide reference points for overlaying the first image and the second image. Thus, it facilitates the generation of a composite image. For details on the overlay of the first and second image, see the section "Image Acquisition and Analysis" below.

In a preferred embodiment, the biological sample is an FFPE tissue sample, the first binder is an antibody for HER2, the optional one or more additional binders is a pan-cytokeratin antibody cocktail, the fluorescent marker is DAPI, and the target nucleic acid sequence is HER2.

Signals from the probe-labeled fluorophores and the fluorescent marker may be detected using a detection system as discussed above. Additional details about the method and system for fluorescent detection, as well as the method and system for generating a second image of the sample are provided hereinbelow under the heading "Image Acquisition and Analysis".

In some embodiments, after the second image of the biological sample is generated from the detected fluorescent signals, the fluorescent signals from the probes for each of the target nucleic acid sequences are modified by, for example, oxidation, stripping, photobleaching, or a mixture thereof. Thereafter, one or more additional images are obtained following the method herein described before. Namely, each additional image is generated by (1) contacting the sample with a probe for each of at least one additional target nucleic acid sequences thus hybridizing the probes with the sequences; (2) optionally, staining the sample with the fluorescent marker; (3) detecting, by fluorescence, signals from the probes for each of the additional sequences and the fluorescent marker; and (4) generating an image of the sample from the detected fluorescent signal.

Image Acquisition and Analysis

In certain embodiments, the method for providing an image of a single biological sample includes generating a first image of the biological sample and generating a second image of the biological sample. These first and second images are generated by (1) fluorescent detection of the signals from the biological sample, and (2) generating the first and second image of the sample from the detected fluorescent signals, respectively. These steps are preferably performed using a fluorescence microscope and repeated for each of the fluorophores used in the contacting and staining steps. Thus, each fluorophore is excited and its fluorescent emission measured at its wavelength using a standard instrument such as a CCD camera or a fluorescent scanner. Optionally, autofluorescence of the biological sample is also measured and its effect on the measurement of certain fluorophore is taken into consideration. For example, an algorithm may be used to subtract out background autofluorescence at one or more emission wavelength.

In certain embodiments, both the first image and the second image of the entire biological sample are obtained at high resolution. Thus, the emission from each fluorophore is measured at its emission wavelength at high resolution. By high resolution, it is meant that the images were obtained at a resolution between 20× to 100×, corresponding to a numerical aperture between 0.5 and 1.4, supporting a pixel size of 75-375 nm. Preferably, the images are obtained at 40×, at a numerical aperture of about 0.85 and pixel size of about 170 nm. Image capture at 40× is preferable since the resolution is high enough to capture the FISH signals while capturing relatively large FOV's compared to a 60× or 100×.

In other embodiments, the biological sample may not occupy the entire surface of the solid support, or a high resolution image of the entire biological sample may not be necessary. Thus, while obtaining the first image, the entire surface of the solid support may be first scanned at a low resolution such as at 2×. An image analysis algorithm is then applied to the low resolution image and detects the area that contains the biological sample. Coordinates that mark the border of the biological sample are captured and used to direct subsequent higher resolution scan(s). The measurement of emission from one of the fluorophore may be sufficient to obtain the coordinates for the border of the sample.

Thus, the area that contains the biological sample may be detected by a computer implemented method comprising: obtaining an image of the biological sample using at least one processor; segmenting the image with the processor into a plurality of regions using either (a) a maximum a posteriori marginal probability (MPM) process with a Markov Random Field (MRF), or (b) a maximum a posteriori (MAP) estimation with a Markov Random Field (MRF); and classifying the plurality of regions into a background region and a tissue region to form a binary mask. The method may also comprise applying an active contour method to the binary mask to refine the biological sample boundary.

In still other embodiments, a higher resolution image of the entire biological sample may not be necessary. Rather, a higher resolution image is only required for selected regions of interest (ROI) of the sample. Thus, while generating the first image, the biological sample is first imaged at a lower resolution (such as at 10×, compared to the higher resolution) which enables ROI selection. Optionally, imaging at lower resolution includes a scan for each of the fluorophores used in the contacting and staining step. One or more ROIs may be selected based on predefined criteria (e.g., sample integrity, phenotype such as tumor or normal, muscle or duct tissue etc.). In certain embodiments, the ROIs are selected based, at least in part, on protein expression level of the target protein(s) detected from the first binder. Thus, certain ROIs may be selected for a lower target protein expression level compared to a first threshold, while other ROIs may be selected due to a higher protein expression level compared to a second threshold (which may be different from the first threshold). The coordinates of the ROIs are used to direct the higher resolution scanning to the ROIs only. In certain embodiments, the second image is obtained for the ROIs alone, at the same higher resolution as the image obtained for the ROIs for the first image.

As described above, in certain embodiments, the initial image (i.e., lower resolution image) is first converted into one or more brightfield type image that resemble a brightfield staining protocol. Thus, the initial fluorescence image data may be used to generate a simulated (virtual/molecular) hematoxylin and eosin (H&E) image via an algorithm. Alternatively, a simulated (virtual/molecular) 3,3'-Diaminobenzidine (DAB) image may be generated via a similar algorithm. Detailed methods for converting fluorescence image data into a brightfield type image is described hereinbelow. The brightfield type image is then used for the selection of the region of interest, based at least in part, on morphological information.

In certain embodiments, the image of the entire biological sample or selected ROIs within the sample may not be obtainable with a single scan due to the limitation of the microscope's field of view (FOV). That is, the area to be imaged may be larger than the microscope FOV can capture. In such cases the desired image may be acquired by capturing multiple FOVs across the slide or selected ROI. These raw images of the FOVs are corrected to adjust for field variation and may be then stitched together according to an algorithm that aligns the separate FOVs into a single image of the entire slide or ROI. Such image stitching algorithms are well-known to a person skilled in the art, see U.S. Pat. No. 6,674,884. Monochrome cameras are often used in fluorescent imaging because of their higher sensitivity and ability to capture predetermined wavelengths by utilizing the appropriate excitation and emission filters along with dichroic mirror. Thus, gray scale images for individual channels are generated. The gray scale digital images for each fluorescent channels may be pseudo-colored and merged to populate the desired image.

In a preferred embodiment, generating the first image comprises (1) optionally generating a lower resolution image of the entire solid support and locating the sample on the solid support; (2) generate a medium resolution image of the sample; (3) identify regions of interest (ROI) according to predetermined criteria; and generating a higher resolution image for each of the ROIs. The second image generated is a higher resolution image of each of the ROIs selected during the generation of the first image. In these embodiments, the term lower, medium and higher is not limited to certain magnifications. Rather, they are relative to each other. In a most preferred embodiment, the low resolution image is a 2× image; the medium resolution image is a 10× image and the high resolution images are 40× images.

In certain embodiments, it may be desirable to enhance the images by computer-aided means to more clearly illustrate the characteristics of the target protein or the target nucleic acid. Thus, one example creates a RGB color blend heatmap image where target protein expression levels are mapped to a reference color lookup table. An example of this lookup table would map low level intensities to shades of blue, intermediate intensities to shades of yellow and high intensities to shades of red for easier identification of areas with different levels of staining intensity. In another example, a color blended composite image is created for the first image, to better display the spatial relationship among the target protein, the morphological binders, as well as the fluorescent marker. For example, a target protein binder would be colored yellow and a morphological binder would be colored blue and so areas where target protein is expressed in the morphological binder marked region, the staining would appear green for easy and specific identification. In still another example, a pseudo-color image of a particular fluorophore channel may be created. For example a FISH signal for a gene of interest would be colored red and another region of the same chromosome would be colored green making it easy to distinguish relative amounts of the two types of signals in a given cell or area of tissue.

In certain embodiments, the first and second images are aligned, preferably according to, at least in part, some of the images obtained from the signals detected from the fluorescent marker. Preferably, the first and second images are overlaid and a composite image is further created. A composite image allows direct comparison of results obtained from the first image with that from the second image on a cell by cell basis.

A composite image may not include the whole of the first or the second image, or all of the signals acquired in the generation of the first image or the second image. Because of shifts in the position of the slide and the microscope stage, the second image may be rotated or translated with respect to the first image, and this rotation or translation must be corrected for aligning or registering the two images prior to producing a composite image.

To register the images, it is preferred to use an identical morphological marker in the first image and the second image. An example of such a marker is DAPI, which labels the cell nuclei and remains in the sample during subsequent bleaching, staining and other processing. The images obtained from the fluorescent marker provide morphological information regarding particular subcellular compartments in both images, and the relative location of said subcellular compartments remains substantially unchanged in the two images. Thus, an algorithm can use this spatial information to establish a coordinate transformation between the first image and the second image by (a) calculating the Fourier transformations of the two images; (b) transforming the amplitude components Fourier transformations into log-polar co-ordinates, creating a translation-invariant signature of each of the two images; (c) applying a second Fourier transform to the two signatures; (d) calculating the correlation function between the two signatures; (e) inverse Fourier transforming the correlation function, solving for rotation and scaling between the two images; (f) applying the rotation and scale to the second image so that both images are rotated and scaled identically; (g) calculating the cross-power correlation function between the identically-scaled images; and (h) inverse Fourier transforming the cross power correlation, yielding the translation between the first image and the second. The translation, rotation and scale are then used to produce identically-aligned (registered) images for compositing. The cross-power correlation is preferred to the conventional product-moment correlation because it is insensitive to intensity differences between the two images and to slowly-varying intensity differences across the field of view of the microscope.

In certain embodiments, the first and the second image, as well as any composite image created are utilized to characterize the expression of the target protein, as well as the target nucleic acid sequences. Thus, the protein expression level may be analyzed by correlating an intensity value of a signal (for example, fluorescence intensity) to the amount of target in the biological sample. A correlation between the amount of target and the signal intensity may be determined using calibration standards. In some embodiments, one or more control samples may be used. By observing the presence or absence of a signal in the samples (biological sample of interest versus a control), information regarding the biological sample may be obtained. For example by comparing a diseased tissue sample versus a normal tissue sample, information regarding the targets present in the diseased tissue sample may be obtained. Similarly by comparing signal intensities between the samples (i.e., sample of interest and one or more control), information regarding the expression of targets in the sample may be obtained.

The target nucleic acid sequence may be analyzed by its presence, absence, expression or amplification level. For the analysis of DNA sequence of interest, the analysis may be focused on signals within the cell nuclei. Thus, when the DNA sequence of interest is detected by FISH, a number of nuclei are preferably first segmented individually, based at least in part on image obtained from the fluorescent marker (e.g., DAPI staining). Within each nucleus, the FISH spots for the target nucleic acid sequence and optionally the FISH spots for the corresponding chromosome (from a chromosome specific probe) are located. The FISH spots are further analyzed. For example, a ratio of the spots is calculated to evaluate the target gene amplification or rearrangement status.

The protein expression data and the nucleic acid analysis data may be further compared to provide a combined dataset.

The methods disclosed herein may find applications in analytic, diagnostic, and therapeutic applications in biology and in medicine. Analysis of cell or tissue samples from a patient, according to the methods described herein, may be employed diagnostically (e.g., to identify patients who have a particular disease, have been exposed to a particular toxin or are responding well to a particular therapeutic or organ transplant) and prognostically (e.g., to identify patients who are likely to develop a particular disease, respond well to a particular therapeutic or be accepting of a particular organ transplant). The methods disclosed herein may facilitate accurate and reliable analysis of a plurality of targets (e.g., disease markers) from the same biologically sample.

In certain embodiments, the first and/or the second fluorescent image are converted into brightfield type images that resemble a brightfield staining protocol. Thus, the fluorescence signal detected from the one or more additional binders that provide morphological information, the fluorescent marker, as well as any autofluorecence of the biological sample may be used to generate a simulated (virtual/molecular) hematoxylin and eosin (H&E) image via an algorithm. Alternatively, a simulated (virtual/molecular) 3,3'-Diaminobenzidine (DAB) image may be generated via a similar algorithm. In certain embodiments, the virtual H&E image includes signals from the fluorescent marker (e.g., DAPI), the at least one additional binder that provides additional morphological information (e.g., anti-pancytokeratin antibody), and autofluorescence. In certain embodiments, the virtual DAB image includes signals from the fluorescent marker and the binder for the target protein (anti-HER2 antibody).

Thus, in certain embodiments, the composite image is a brightfield type image, such as a virtual H&E or virtual DAB image.

Methods for converting fluorescent images into a pseudo brightfield image are known. Also known is a method that creates a brightfield image from fluorescent images wherein structural features and details of the biological sample are identified as if the image was obtained directly from a specified brightfield staining protocol. U.S. patent application Ser. No. 12/569,396. In certain embodiments of the current invention, an improved method for generating a brightfield type image that resembles a brightfield staining protocol of a biological sample is used, as described more fully in K. Kenny U.S. patent application Ser. No. 13/211,725 entitled "SYSTEM AND METHODS FOR GENERATING A BRIGHTFIELD IMAGE USING FLUORESCENT IMAGES" and filed on Aug. 17, 2011, herein incorporated by reference in its entirety. The method involves the use of a calibration function obtained from a bright-field image of a biological sample or defined using a preselected or desired color. The preselected or desired color may be chosen by an operator, which may be a pathologist or microscopist familiar with standard biological staining protocols. The calibration function estimates an intensity transformation that maps the fluorescent images into the brightfield color space using three parameters, a[Red], a[Green], a[Blue], called the "extinction coefficients.".

The estimated parameters may be derived by preparing one or more biological specimens with a wide range of staining intensity in the biomarker of interest, labeled with a visible dye such as hematoxylin, eosin, or diaminobenzidine (DAB). The sample may then be imaged in brightfield, and the distribution of red, green, and blue pixel intensity levels may be calculated; the pixel intensity levels are normalized to the interval [0,1]. The color with the smallest value for mean(log intensity) is identified. Without loss of generality, one may presume a specific color. For example, if the color is green, the mean values of (log Red/log Green) and (log Blue/log Green) are calculated, and the triple, (mean[log Red/log Green], 1, mean[log Blue/log Green]) are used as extinction coefficients.

Alternatively, the extinction coefficients may be derived without reference to an actual brightfield dye. Instead, a designer may choose a color that should be used for a moderately intense stain. If that color is (R, G, B) in a linear color model wherein the channels R, G, and B are normalized to the interval [0,1], then the extinction coefficients are simply (log R, log G, log B). This approach allows the method to simulate a bright-field stain using a dye that does not exist in nature.

The correspondence of the points in the fluorescent images may then be established by two methods: intensity-based and feature-based.

In a feature-based method, the image of the nuclei, epithelia, stroma or any type of extracellular matrix material may be acquired for both the fluorescent image and the bright-field image. The feature-based structure may be selected using a manual process or automatically. Corresponding structures are selected in images from both modalities. For the fluorescent image, the image may be captured using a fluorescent microscope with an appropriate excitation energy source tuned to a given biomarker and with filters appropriate for collecting the emitted light. A brightfield image of the sample may then be obtained which may then be segmented into Red (R), Green (G) and Blue (B) channels and the color and intensity of the feature-based structure measured.

In an intensity-based method, location of the sample area under the microscope may be controlled with electronic, magnetic, optical or mechanical sensors so that the sample area can be repeatedly located close to the same position for the next image acquisition. Intensity based registration is generally applicable to a broad class of biomarkers. Generally, the biological sample, which is fixed or otherwise provided on a substrate such as, but not limited to, a TMA, a slide, a well, or a grid, is labeled with molecular biomarkers, and imaged through a fluorescent microscope.

In either the intensity-based or feature-based method, the transformation from the fluorescent images to the brightfield color space uses the estimated mapping parameter in a nonlinear transformation equation. The nonlinear transformation equation may be represented using the red, green, blue values or color space (R, G, B) and the transformation represented by the formulas:

$$R = 255 \exp(-a[Dye1]*z[Dye1] - a[Dye2]z[Dye2] - \ldots)$$

$$G = 255 \exp(-b[Dye1]*z[Dye1] - b[Dye2]z[Dye2] - \ldots)$$

$$B = 255 \exp(-c[Dye1]*z[Dye1] - c[Dye2]z[Dye2] - \ldots)$$

In the formulas, the scalars z[Dye1], z[Dye2], ... are the fluorescent dye quantities observed at a given pixel location. The triples (a[Dyen], b[Dyen], c[Dyen]) are a constant times the extinction coefficients of the nth dye in the virtual stain as defined using a preselected or desired color. The constant is chosen so that the output color values (R, G, B) display a readable range of contrast in the image. R, G, and B are resulting red, green and blue pixel values in the brightfield type image; z is a scaling coefficient for a fluorescent dye quantities observed at a given pixel location; and a, b, and c are the extinction coefficients corresponding to the brightfield color space, and wherein the triples a[Dyen], b[Dyen], c[Dyen], are a constant times the extinction coefficients of the nth dye in the virtual stain as defined using a preselected or desired color.

Preferably, the 0.995 quantiles are found for z[Dye1], z[Dye2], ..., and the constants are chosen such that:

$$\min(\exp(-a[Dyen]*z[Dyen]), \exp(-b[Dyen]*z[Dyen]), \exp(-c[Dyen]*z[Dyen])) = 1/255.$$

This causes the dynamic range of the output color to nearly fill the possible dynamic range of an 8-bit image, and results in an intense contrast.

A sharpening transform may be applied to the virtual stain image after it is synthesized. In one embodiment, the sharpening transform may be implemented as a linear convolution filter whose kernel is the matrix:

$$\begin{bmatrix} -0.25 & -0.25 & -0.25 \\ -0.25 & 3.00 & -0.25 \\ -0.25 & -0.25 & -0.25 \end{bmatrix}$$

Applying the sharpening transform gives the output image a crisper appearance with sharper edges and more visible fine details.

Once the transformation parameters are calculated, one or more selected areas of the sample may be used for transformation from a set of fluorescent images into a VSI using the virtual H&E mapping or a similar visual image such as brown DAB staining. The molecular biomarkers advantageously provide functional and compartmental information that is not visible using a brightfield image alone. For example, image analysis algorithms can benefit from the added channels to separate the sample compartments while still providing a pathologist or operator image intensity values representative of a brightfield modality (H&E). For example, a VSI representative of a DAB staining protocol for keratin would show cell nuclei in shades of purple and the cytoskeleton of epithelial cells and fibroblasts in shades of brown.

Alternatively, once the mapping parameters are estimated, the transformation algorithm may be applied to other fluorescent images to generate a VSI. The other fluorescent images may be from a different area of the same biological sample. Alternatively, the other fluorescent images may be from a different biological sample. The different biological sample may include a collection of similar cells obtained from tissues of biological subjects that may have a similar function.

Thus, the method for generating a brightfield type image comprises the steps of acquiring image data of two or more fluorescent images of a fixed area on a biological sample, analyzing the image data utilizing, at least in part, feature-based information or pixel intensity data information to generate mapping parameters wherein the mapping parameters comprises a nonlinear estimation model, applying the mapping parameters to the fluorescent images, transforming the two or more fluorescent imaging into a brightfield color space and generating a brightfield type image. The method may further include applying a sharpening transformation correction to the brightfield type image.

In another aspect of the invention, it is provided a method of analyzing a biological sample, comprising providing a composite image of the biological sample according to methods hereinbefore described, and analyzing the expression of the protein and the nucleic acid sequences of interest from the composite image. In certain embodiments, the method of analyzing a biological sample further comprises creating a RGB color blend heatmap image of the target protein expression level by mapping the fluorescent signal from the first binder to a reference color lookup table. In other embodiments, the method of analyzing a biological sample further comprises creating a color blended composite image for the first image, the composite image includes the image of the target protein, the morphological information represented by the at least one additional binder, and the fluorescent marker. In certain embodiments, the biological sample comprises a cell or a tissue sample. In still further embodiments, the biological sample comprises a Formalin-Fixed, Paraffin-Embedded (FFPE) tissue sample. Thus, in a preferred embodiment, the sample is an FFPE tissue sample, the first binder is an antibody for HER2, the one or more additional binders is a pan-cytokeratin antibody cocktail, the fluorescent marker is DAPI, and the nucleic acid sequence of interest is HER2.

In still another aspect of the invention, it is provided a kit for the fluorescent detection of a protein as well as a target nucleic acid sequence on the same biological sample. Thus, an embodiment of the invention provides a kit that includes components for fluorescent detection of a protein as well as a target nucleic acid sequence on the same biological sample.

In yet another aspect of the invention, it is provided a system for the fluorescent detection of a protein as well as a target nucleic acid sequence on the same biological sample. Thus, one embodiment of the invention provides a system that includes means for performing fluorescent detection of a protein as well as a target nucleic acid sequence on the same biological sample.

In carrying out the methods described it is to be understood that reference to particular buffers, media, reagents, cells, culture conditions, pH and the like are not intended to be limiting, but are to be read so as to include all related materials that one of ordinary skill in the art would recognize as being of interest or value in the particular context in which that discussion is presented. For example, it is often possible to substitute one buffer system or culture medium for another and still achieve similar, if not identical, results. Those of skill in the art will have sufficient knowledge of such systems and methodologies so as to be able, without undue experimentation, to make such substitutions as will optimally serve their purposes in using the methods and procedures disclosed herein. It will be readily apparent to one skilled in the art that varying substitutions and modifications may be made to the invention disclosed herein without departing from the scope and spirit of the invention.

EXAMPLES

The following examples are intended only to illustrate methods and embodiments in accordance with the invention, and as such should not be construed as imposing limitations upon the claims.

Example 1

In one implementation of this invention, breast cancer tissue was obtained from routine histology specimen by standard histology methods: Small part of a surgically resected tumor was fixed in 10% neutral buffered formalin for 8 hours, and then dehydrated by passage of series of solutions with increasing ethanol concentration (50%, 75%, 80%, 95%, 100%) followed by xylene. The sample was then embedded in paraffin and sections of four micrometer thickness were sectioned using a microtome. Sections were floated onto a waterbath and collected one at a time onto a standard microscope slide. The slides were allowed to dry and baked for 2 hours in a 60° C. oven and then deparaffinized by passage through xylene, then re-hydrated by passage through ethanol followed by a series of water-ethanol mixtures with decreasing ethanol concentration, and finally washed with PBS. Next, the slide was subjected to antigen retrieval procedure by heating the slide in Bond Epitope Retrieval solution (Leica) at 100° C. for 20 min. Slide was then stained with Her2 antibody conjugated with Cy5 combined with a cocktail of Cytokeratin antibodies conjugated with Cy3, followed by counterstaining with DAPI. The slide was coverslipped and entire slide area was imaged using fluorescence microscope equipped with 1.25× magnification objective and a DAPI filterset. The images were captured using a digital monochrome camera, and then computationally combined to form one stitched image of the entire slide. From this stitched full slide image location of the tissue section was determined, and coordinates for imaging tissue section only were recorded. This method significantly shortens the time necessary to collect subsequent images.

10× Images of the tissue section area were then collected using DAPI, Cy3 and Cy5 filtersets to get images specific for nuclei, Cytokeratins and Her2 protein staining, respectively. These individual marker images were stitched to form one image and then overlaid to form a fluorescence pseudocolor image as well as virtual H&E and virtual DAB images. Stitched, combined images allowed a pathologist to select regions of interest from the tissue section to specifically contain invasive tumor. Coordinates for these invasive tumor regions were recorded and used to collect images using 40× magnification and filtersets for all fluorophores, including DAPI, as before.

To allow subsequent FISH staining coverslip was removed by incubation in 2×SSC buffer and slide was subjected to 10 min treatment with 0.05% pepsin that partially removed protein structures to allow access to nuclear DNA. Slide was then fixed using aqueous 4% formaldehyde solution for 10 min, washed and subjected to hybridization using FISH probes for Her2 gene labeled with SpectrumOrange and chromosome 17 centromere labeled with SpectrumGreen (Abbott Molecular, DesPlaines, Ill.). The hybridization was carried out by dehydrating the slide by passage through series of aqueous solutions of increasing concentration of ethanol followed by 100% ethanol and then allowed to dry briefly. The probe mixture was applied on the region of the slide containing tissue section, then covered with a coverslip and placed in a slide incubator capable of heating and cooling the slide. The slide containing the probe mixture was heated to 80° C. for 10 min to denature DNA hybrids and allowed to cool to 37° C. The slide was then kept at that temperature for 16 hours. Slide was then washed in 2×SSC buffer containing 0.3% of detergent NP-40 and washed 2 min in 2×SSC containing 0.3% NP-40 at 72° C. followed by counterstaining with DAPI. Next, the regions of tissue section that had invasive tumor were imaged using coordinates recorded in the immunofluorescence step. Image sets were recorded at 40× using filtersets specific to SpectrumOrange, SpectrumGreen and DAPI.

Figure 2A:
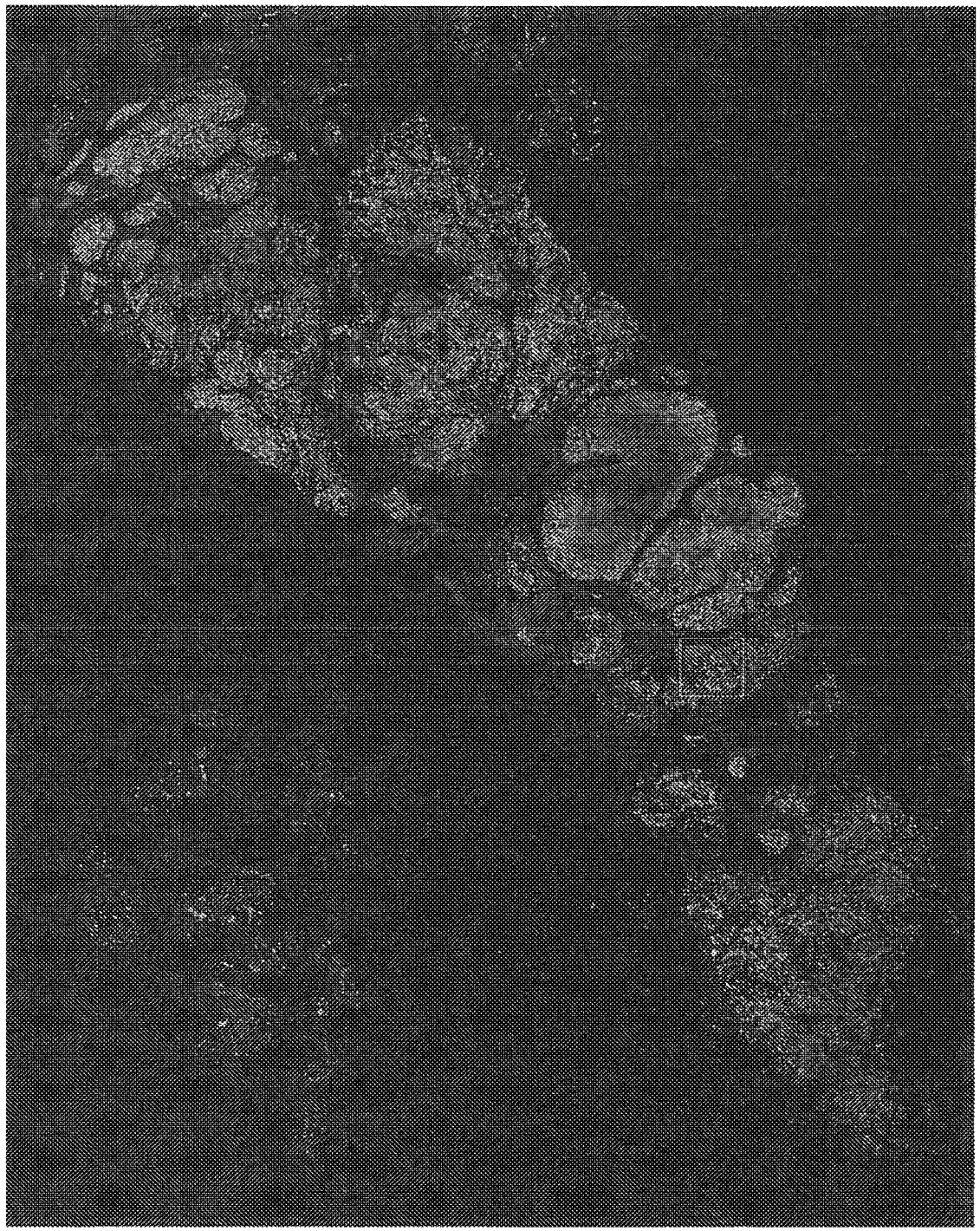
FIG. 2A: Pseudocolor image illustrating a breast cancer tissue imaged at 10×. Tissue section was stained using Cy3 labeled Cytokeratin antibodies, Cy5 labeled Her2 antibody and DAPI. Immunofluorescence images were collected with monochrome camera, digitally overlaid and colored as follows: DAPI, blue; Cytokeratins, green; Her2, red. Selection of an ROI, shown in FIG. 2 is shown with a light blue rectangle.
Figure 2B:
FIG. 2B: DAPI and cytokeratin Images from FIG. 1A and an image representing background fluorescence in green channel were converted to form a virtual H&E image as described.
Figure 2C:
FIG. 2C: Virtual DAB image generated from DAPI and Her2 images in 1A.
Figure 3:
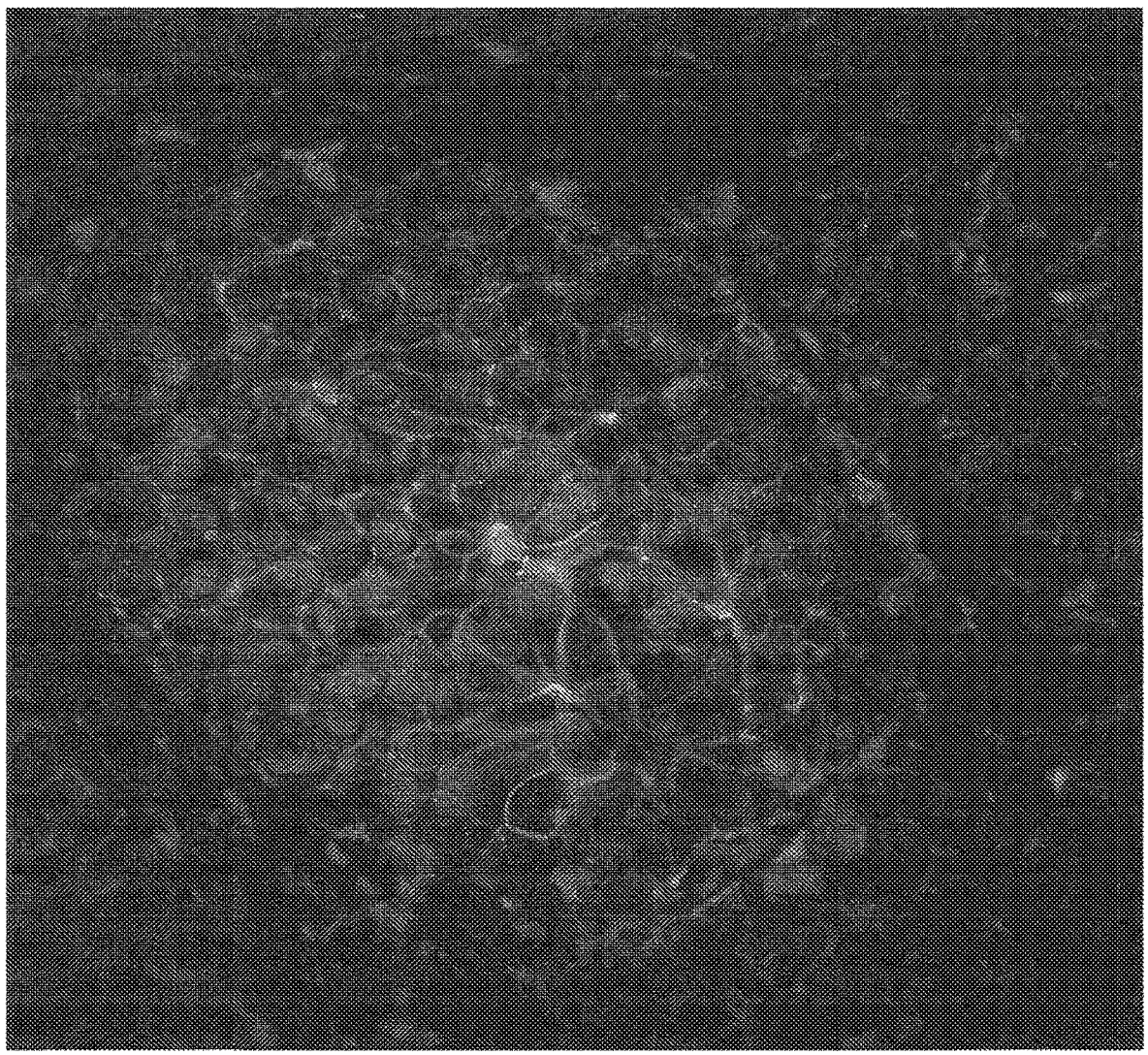
FIG. 3: Combined Her2 Immunofluorescence (yellow), DAPI (blue), Her2 FISH (red) and Centromere 17 FISH (green) of a 40×ROI selected from tissue shown in FIG. 2.

Immunofluorescence image sets and FISH image sets were then aligned using DAPI images from each round, respectively and then overlaid and visualized using specialized visualization software (FIGS. 2 and 3). This method allows precise identification of the invasive tumor area and cell to cell comparison of Her2 protein expression and gene amplification. Previous practice methods limit comparison of immunostaining and FISH between serial sections, where direct cell to cell correlations cannot be made.

Example 2

In a second implementation a lung cancer tumor biopsy was obtained on a glass slide and deparaffinized, hydrated and antigen retrieved as above. The slide was then stained using antibodies for Cytokeratin-7 and EGFR conjugated with Cy3 and Cy5, respectively followed by staining with DAPI. The tissue section was imaged using fluorescence microscope at 20× magnification and recorded using a digital camera. Representative areas of the tissue section were imaged using filtersets for Cy5, Cy3 and DAPI. Slide was then subjected to dye inactivation procedure as described more fully in U.S. patent application Ser. No. 13/336,409 entitled "PHOTOACTIVATED CHEMICAL BLEACHING OF DYES FOR USE IN SEQUENTIAL ANALYSIS OF BIOLOGICAL SAMPLES" and filed on Dec. 23, 2011, herein incorporated by reference in its entirety, and stained with antibodies for NaKATPase and IFG1R conjugated with Cy3 and Cy5, respectively and was counterstained with DAPI. Tissue section was aligned so that images would be collected on same regions as on the previous round, and imaged again using 20× magnification on each fluorescence channel as above.

Slide was then subjected to pepsin treatment and fixation as in the previous example and then hybridized with FISH probes for EGFR (PlatinumBright415), cMet (Platinum- Bright550) and Chromosome 7 centromere (Platinum-Bright495) and counterstained with DAPI. Selected regions of the tumor area, contained within the areas obtained in immunofluorescence imaging rounds were imaged at 40× using filtersets specific for DAPI and blue, green and red fluorophores. Sections of all imaging rounds were then registered using DAPI images of each of the imaging round sets to align the images and combined in single field images to allow simultaneous visualization of cell by cell compartments of nucleus, cytoplasm and cell membrane as well as expression of EGFR and IFG1R proteins (data not shown). The image also allowed visualization of FISH signals for cMet and EGFR genes thus allowing correlation of possible gene amplification and protein overexpression on the same tissue section (data not shown).

Example 3

In another implementation of this invention, a tumor section on a microscope slide is subjected to deparaffinization and rehydration, followed by antigen retrieval as described above. The sample is stained with Cy3 conjugated Cytokeratin-7 antibody combined with Cy5 conjugated EGFR antibody and counterstained with DAPI. The sample in its entirety is imaged using DAPI, Cy3 and Cy5 filtersets, and the images are digitally recorded. After dye inactivation that sample is stained with a second set of markers, namely Cy5 conjugated NaKATPase antibody and Cy3 conjugated IGF1R antibody and counterstained with DAPI. The sample is imaged on the same positions as in the first round using DAPI, Cy3 and Cy5 filtersets and the images is digitally stored as above.

The sample is then subjected to pepsin digestion and hybridization with DNA probes for Her2 and Centromere of chromosome 17 and DAPI counterstain as described in the first example above. The sample is then imaged using a fluorescence microscope with filtersets for each of the FISH probes and DAPI and images is stored digitally.

The sample is then subjected to dye inactivation followed by second round of FISH hybridization with a probeset for EGFR and centromere of chromosome 7. This is carried out by dehydrating the slide by passage through series of aqueous solutions of increasing concentration of ethanol followed by 100% ethanol and then allowed to dry briefly. The second probe mixture is applied on the region of the slide containing tissue section, then covered with a coverslip and placed in a slide incubator capable of heating and cooling the slide. The slide containing the probe mixture is heated to 80° C. for 10 min to denature DNA hybrids and to remove inactivated probe from first FISH round. The slide is then allowed to cool to 37° C. and then kept at that temperature for 16 hours. Slide is then washed in 2×SSC buffer containing 0.3% of detergent NP-40 and washed 2 min in 2×SSC containing 0.3% NP-40 at 72° C. followed by counterstaining with DAPI.

The slide is then imaged using filtersets for second set of FISH probes and DAPI. All of the imaging rounds are then aligned using DAPI images, and FISH and IF signals are analyzed for gene expression from IF images and gene amplification from FISH channels. This allows cell to cell correlation of multiple rounds of IF staining and thus expression status of multiple protein markers and multiple rounds of FISH staining and so amplification status of multiple genes.

While the particular embodiment of the present invention has been shown and described, it will be obvious to those skilled in the art that changes and modifications may be made without departing from the teachings of the invention. The matter set forth in the foregoing description and accompanying drawings is offered by way of illustration only and not as a limitation. The actual scope of the invention is intended to be defined in the following claims when viewed in their proper perspective based on the prior art.

We claim:

1. A method of generating a composite image of a region of interest in a human tissue sample comprising the steps of:
    1) generating a first image including said region of interest of said sample having undergone a first protocol but not a second protocol, wherein the first protocol comprises: (i) binding a human target protein-specific monoclonal antibody labeled with a fluorophore to the human target protein in the sample, wherein said human target protein is selected from the group consisting of EGFR, Her2, ALK, galactosyl transferase II, neuron specific enolase, proton ATPase-2, acid phosphatase, Ki67, cyclin E, p53 and cMet; (ii) detecting by immunofluorescence the bound fluorophore to generate the first image, and (iii) staining the sample with a fluorescent marker that provides morphological information, and;
    2) digesting said sample with a protease after generating the first image but before said sample has undergone the second protocol;
    3) generating a second image including said region of interest of said sample after having undergone the second protocol, wherein the second protocol comprises: (i) hybridizing a nucleic acid probe labeled with a fluorophore to a target nucleic acid in the sample, wherein the target nucleic acid encodes a selective portion of the human target protein; and (ii) detecting by immunofluorescence the hybridized probe fluorophore to generate the second image wherein the nucleic acid probe is a DNA or RNA of from 4 to 50 nucleotides; and
    4) generating a composite image that includes at least the region of interest from each of the first and the second images by registering fluorescent signals from the first image with fluorescent signals from the second image and aligning and overlaying the first and second images based on the morphological information.

2. The method of claim 1, wherein the region of interest is selected by comparing the first image of the tissue sample to pre-determined criterion.

3. The method of claim 1, wherein the first protocol further includes immunofluorescence detection of at least one additional protein wherein the additional protein provides the morphological information.

4. The method of claim 1, wherein said hybridizing reaction is selected from the group consisting of FISH, IQ-FISH, in-situ PCR, rolling circle amplification and primed in situ labeling.

5. The method of claim 1, wherein the second protocol comprises staining the sample with a fluorescent marker that provides morphological information.

6. The method of claim 5, wherein said fluorescent marker stains the nucleus of a cell.

7. The method of claim 1, wherein at least one of the first or the second protocol comprises detecting autofluorescence of the tissue sample.

8. The method of claim 1, wherein the first and second images are fluorescent images.

9. The method of claim 8, wherein generating the first image and/or generating the second image comprises generating a brightfield type image.

10. A method of analyzing a human tissue sample, comprising providing an image of the sample according to claim 1, and analyzing protein expression and nucleic acids of the sample from the image.

11. The method of claim 1, wherein said second image covers a smaller area of said sample compared to an area of said sample covered by said first image.

* * * * *